United States Patent
Gudim et al.

(10) Patent No.: US 11,609,230 B2
(45) Date of Patent: Mar. 21, 2023

(54) HIGHLY SENSITIVE PARTICLE ENHANCED ASSAY FOR THE QUANTIFICATION OF NT-PROBNP

(71) Applicant: Gentian AS, Moss (NO)

(72) Inventors: Ingvild Gudim, Moss (NO); Torsten Knüttel, Ski (NO); Berit Løseth, Oslo (NO); Christian Melbø-Jørgensen, Moss (NO); Tom Nilsen, Moss (NO); Erling Sundrehagen, Moss (NO); Ly Thi Tran, Moss (NO); Jie Yang, Drammen (NO)

(73) Assignee: Gentian AS, Moss (NO)

( * ) Notice: Subject to any disclaimer, the term of this patent is extended or adjusted under 35 U.S.C. 154(b) by 0 days.

(21) Appl. No.: 17/490,568

(22) Filed: Sep. 30, 2021

(65) Prior Publication Data
US 2022/0042978 A1 Feb. 10, 2022

Related U.S. Application Data

(63) Continuation of application No. PCT/EP2020/072720, filed on Aug. 13, 2020.

(30) Foreign Application Priority Data

| Aug. 13, 2019 | (SE) | 1950929-8 |
| Feb. 12, 2020 | (SE) | 2050150-8 |

(51) Int. Cl.
| G01N 33/543 | (2006.01) |
| C07K 16/26 | (2006.01) |
| G01N 21/17 | (2006.01) |
| G01N 33/74 | (2006.01) |

(52) U.S. Cl.
CPC ....... *G01N 33/54313* (2013.01); *C07K 16/26* (2013.01); *G01N 21/17* (2013.01); *G01N 33/74* (2013.01); *C07K 2317/23* (2013.01); *C07K 2317/34* (2013.01); *C07K 2317/92* (2013.01); *G01N 2333/58* (2013.01); *G01N 2800/325* (2013.01)

(58) Field of Classification Search
None
See application file for complete search history.

(56) References Cited

U.S. PATENT DOCUMENTS

| 2005/0148024 A1 | 7/2005 | Buechler |
| 2005/0287613 A1 | 12/2005 | Jackowski et al. |
| 2008/0312152 A1 | 12/2008 | Pollitt et al. |
| 2009/0163415 A1 | 6/2009 | Katrukha et al. |
| 2010/0062474 A1 | 3/2010 | Peter |
| 2012/0009174 A1 | 1/2012 | Van Eyk et al. |
| 2014/0045714 A1 | 2/2014 | Gerszten et al. |
| 2019/0226988 A1* | 7/2019 | Iwamoto ............... G01N 21/64 |

FOREIGN PATENT DOCUMENTS

| CN | 205484063 U | 8/2016 | |
| CN | 108613977 A | 10/2018 | |
| CN | 109942707 A | 6/2019 | |
| WO | WO-2005/121792 A1 | 12/2005 | |
| WO | WO-2007/110779 A2 | 10/2007 | |
| WO | WO2010132481 A1 * | 11/2010 | ............ C07K 16/26 |
| WO | WO-2011/030286 A1 | 3/2011 | |
| WO | WO-2011/062931 A1 | 5/2011 | |

OTHER PUBLICATIONS

Semenov et al., Analytical issues with natriuretic peptides—has this been overly simplified?, The Journal of the International Federation of Clinical Chemistryand Laboratory Medicine, Jul. 1, 2016, 27(3), pp. 189-207. (Year: 2016).*

"Elecsys proBNP II," Sep. 1, 2018, available <https://www.rochecanada.com/content/dam/rochexx/roche-ca/products/docs/package_inserts/ElecsysproBNPII-04842464190-EN-V13-CAN.pdf>, (7 pages).

Blirup-Jensen et al., "Protein standardization IV: Value transfer procedure for the assignment of serum protein values from a reference preparation to a target material," Clin Chem Lab Med. 39(11):1110-22 (2001).

Dolgin, *Nomenclature and criteria for diagnosis of diseases of the heart and great vessels*, 9th ed. Boston, MA: Lippincott Williams and Wilkins; Mar. 1, 1994. Abstract only.

Foo et al., "Circulating fragments of N-terminal pro-B-type natriuretic peptides in plasma of heart failure patients," Clin Chem. 59(10):1523-31 (2013).

Geysen et al., "Use of peptide synthesis to probe viral antigens for epitopes to a resolution of a single amino acid," Proc Natl Acad Sci U S A. 81(13):3998-4002 (1984).

Halfinger et al., "Unraveling the Molecular Complexity of O-Glycosylated Endogenous (N-Terminal) pro-B-Type Natriuretic Peptide Forms in Blood Plasma of Patients with Severe Heart Failure," Clin Chem. 63(1):359-68 (2017).

International Search Report and Written Opinion for International Application No. PCT/EP2020/072720, dated Nov. 13, 2020 (19 pages).

Januzzi et al., "NT-proBNP testing for diagnosis and short-term prognosis in acute destabilized heart failure: an international pooled analysis of 1256 patients: the International Collaborative of NT-proBNP Study," Eur Heart J. 27(3):330-7 (2006).

(Continued)

*Primary Examiner* — Gary Counts
(74) *Attorney, Agent, or Firm* — Clark & Elbing LLP

(57) ABSTRACT

NT-proBNP can be determined in a biological sample using at least one antibody which recognizes an epitope of NT-proBNP in both a glycosylated and non-glycosylated form of NT-proBNP. Said antibody is preferably an isolated polyclonal antibody or a mixture of monoclonal antibodies coated onto a particle, preferably coated onto said particle in a coating ratio of 6-60%, forming a layer or multiple layers of antibodies on said particle. The assay, realized in the form of a nephelometric or turbidimetric assay, can be applied to a wide range of automated clinical analyzers.

10 Claims, 10 Drawing Sheets

Specification includes a Sequence Listing.

(56) References Cited

OTHER PUBLICATIONS

Langedijk et al., "Helical peptide arrays for lead identification and interaction site mapping," Anal Biochem. 417(1):149-55 (2011).
Newman et al., "Particle enhanced light scattering immunoassay," Ann Clin Biochem. 29(Pt 1):22-42(1992).
Notice for Swedish Application No. 1950929-8, dated Jan. 30, 2020 (12 pages).
Prontera et al., "Comparison between analytical performances of polyclonal and monoclonal electrochemiluminescence immunoassays for NT-proBNP," Clin Chim Acta. 400(1-2):70-3 (2009).
Røsjø et al., "Influence of glycosylation on diagnostic and prognostic accuracy of N-terminal pro-B-type natriuretic peptide in acute dyspnea: data from the Akershus Cardiac Examination 2 Study," Clin Chem. 61(8):1087-97 (2015).
Saenger et al., "Specificity of B-Type Natriuretic Peptide Assays: Cross-Reactivity with Different BNP, NT-proBNP, and proBNP Peptides," Clin Chem. 63(1):351-8 (2017).
Schellenberger et al., "The precursor to B-type natriuretic peptide is an O-linked glycoprotein," Arch Biochem Biophys. 451(2):160-6 (2006).
Seferian et al., "Immunodetection of glycosylated NT-proBNP circulating in human blood," Clin Chem. 54(5):866-73 (2008).
Semenov et al., "Processing of pro-brain natriuretic peptide is suppressed by O-glycosylation in the region close to the cleavage site," Clin Chem. 55(3):489-98 (2009).
"TechNotes: Human proBNP, BNP and NT-proBNP," HyTest Ltd., <https://shop.hytest.fi/spree/products/2930/Human_proBNP_BNP_and_NT-proBNP_TechNotes.pdf?1560756922>, retrieved on Jul. 8, 2019 (16 pages).
Timmerman et al., "Functional reconstruction and synthetic mimicry of a conformational epitope using CLIPS™ technology," J Mol Recognit. 20(5):283-99 (2007).

* cited by examiner

His Pro Leu Gly Ser Pro Gly Ser Ala Ser Asp Leu Glu Thr Ser Gly Leu Gln Glu Gln
1           5          10          15          20
Arg Asn His Leu Gln Gly Lys Leu Ser Glu Leu Gln Val Glu Gln Thr Ser Leu Glu Pro
            25          30          35          40
Leu Gln Glu Ser Pro Arg Pro Thr Gly Val Trp Lys Ser Arg Glu Val Ala Thr Glu Gly
            45          50          55          60
Ile Arg Gly His Arg Lys Met Val Leu Tyr Thr Leu Arg Ala Pro Arg    (SEQ ID NO 1)
            65          70          75

HIGHLY SENSITIVE PARTICLE ENHANCED ASSAY FOR THE QUANTIFICATION OF NT-PROBNP

TECHNICAL FIELD

This disclosure relates to the field of diagnostic assays, and in particular to a novel assay for determination of a concentration of N-terminal pro-hormone BNP (NT-proBNP) in a sample, including antibodies, immunoparticles, reagents and calibrators for performing such assay.

SEQUENCE LISTING

The instant application contains a Sequence Listing which has been submitted electronically in ASCII format and is hereby incorporated by reference in its entirety. Said ASCII copy, created on Sep. 30, 2021 is named "51398-006001 Sequence_Listing" and is 2,455 bytes in size.

BACKGROUND

Brain natriuretic peptide, also known as B-type natriuretic peptide, abbreviated BNP, is a hormone secreted by cardiomyocytes in the heart ventricles in response to stretching caused by increased ventricular blood volume, cardiac wall stress. NT-proBNP is produced by cleaving the proBNP into BNP and the NT-proBNP. See FIG. 1.

Measuring BNP and NT-proBNP is useful in the diagnosis and monitoring of heart failure. BNP and NT-proBNP cannot be compared directly, as BNP is the biological active metabolite and has a half-life ($t_{1/2}$) of approx. 20 min and does not degrade in the kidneys. It is only stable for a very short time in vitro.

NT-proBNP is however more stable, it is biologically inactive and filtered by the kidneys. Its half-life is about 1 to 2 hours and the concentration in the blood is higher than that of BNP. Compared to BNP, the half-life is highly dependent of kidney function. In vitro, NT-proBNP is more stable than BNP, and can be stored for at least three days at 2-8° C. Consequently, proBNP and NT-I.

proBNP are used as gold standard clinical markers of myocardial dysfunction such as cardiac hypertrophy and left ventricle heart failure.

The recommended cut-off to exclude heart failure in patients with non-acute symptoms is 35 ng/L and 125 ng/L for BNP and NT-proBNP respectively. The recommended cut-off to exclude heart failure in patients with dyspnea or increasing symptoms is higher, 100 ng/L and 300 ng/L for BNP and NT-proBNP respectively. The reference range is however wide, in particular for acute heart failure, and in particular for older patients, see Table 1:

TABLE 1

Age-stratified cut-offs for the diagnosis of acute heart failure

| Age | Cut-off | Sensitivity, % |
|---|---|---|
| <50 years | <450 pg/mL | 97 |
| 50-75 years | <900 pg/mL | 90 |
| >75 years | <1800 pg/mL | 85 |

(Januzzi et al., NT-proBNP testing for diagnosis and short-term prognosis in acute destabilized heart failure: an international pooled analysis of 1256 patients. Eur Heart J 2006; 27: 330-37)

NT-proBNP is a peptide chain of 76 amino acids with a mass of 8458 Da in its non-glycosylated form. The amino acid sequence is shown in FIG. 2. Before 2006, the glycosylation of proBNP was unknown. The first evidence of proBNP glycosylation was published in 2006 (Schellenberger, U. et al., The precursor to B-type natriuretic peptide is an O-linked glycoprotein, Arch Biochem Biophys. 2006 Jul. 15; 451(2):160-6. Epub 2006 Apr. 19). The presence of glycosylation and the observations of higher molecular weight isoforms of BNP have caused much confusion about the relevant forms of NT-ProBNP in the blood stream.

In 2015, it was shown that higher NT-proBNP concentrations were measured using the proBNP II assay on an Elecsys® platform (Roche Diagnostics) when the samples were pretreated with a deglycosylation enzyme (Rosjo et al., Influence of glycosylation on diagnostic and prognostic accuracy of N-terminal pro-B-type natriuretic peptide in acute dyspnea: data from the Akershus Cardiac Examination 2 Study, Clin Chem, 2015 August; 61(8):1087-97. doi: 10.1373/clinchem.2015.239673. Epub 2015 Jun. 8).

The exact glycosylation sites of endogenous proBNP and NT-proBNP were only recently characterized (Halfinger, B. et al., Unravelling the Molecular Complexity of 0-Glycosylated Endogenous (N-Terminal) pro-B-Type Natriuretic Peptide Forms in Blood Plasma of Patients with Severe Heart Failure. Clinical Chemistry. 2017, Vol. 63, 1).

Sandwich immunoassays for the detection of NT-proBNP are commercially available, and disclosed for example in EP 1151304 (Roche Diagnostics GmbH) which relates to a sandwich assay using two antibodies which recognize different epitopes of the native NT-proBNP and at the same time can bind to said native NT-proBNP, wherein the at least two antibodies bind in the region of amino acid 10-50 of N-terminal proBNP and the antibodies are obtained by immunizing a suitable organism with recombinant NT-proBNP.

EP 1625163, EP 1625164 and EP 2256132 (Roche Diagnostics GmbH) define antibodies specific to epitopes on the proBNP molecule defined by amino acids no. 38-43, 42-46, 39-66, 40-47, 41-48 and 42-49.

U.S. Pat. Nos. 9,034,591 and 9,145,459 (HyTest Ltd.) both relate to an immunoassay kit for detecting BNP, proBNP, or a fragment thereof, in a sample, comprising: a first antibody, or binding fragment thereof, specific for a region of a ring structure of BNP and proBNP; wherein the first antibody, or binding fragment thereof, binds to BNP, proBNP, or to a fragment thereof comprising the region thereof so as to form a first order immune complex; and a second antibody, or binding fragment thereof, not recognizing free BNP, free proBNP, or a free fragment thereof, or free first antibody, or which recognizes them with 10-fold or less affinity than it recognizes the first order immune complex, wherein, the second antibody, or binding fragment thereof, is Ab-BNP2 or Ab-BNP4.

EP2084544B1 (HyTest Ltd.) relates to stable standards for BNP immunoassays, and defines the use of a peptide selected from the group consisting of an isolated or recombinant or synthetic proBNP consisting of a specific amino acid sequence or a sequence that differs by five or fewer amino acid substitutions, insertions or deletions as a standard or calibrator in a method for detecting BNP immunoreactivity in a sample.

EP2251356B1 (*Nexus* DX Inc.) relates to a polyclonal-monoclonal ELISA assay for detecting N-terminal proBNP using isolated polyclonal antibodies specific for NT-proBNP within a certain range of amino acid residues, and isolated monoclonal antibodies specific for NT-proBNP within another, specific range of amino acid residues.

Based on the above, a need still exists in the field to quickly determine the correct or true NT-proBNP concentration by a sensitive method.

SUMMARY

The present inventors solve the problem that currently available assays are not sufficiently sensitive and most likely underestimate the true NT-proBNP concentrations by providing an improved particle-enhanced immunoassay for the quantification of NT-proBNP.

NT-proBNP, the N-terminal region of proBNP that consists of 76 amino acids and six (seven) O-glycosylation sites, has the following amino acid sequence:
HPLGSPGSAS DLETSGLQEQ RNHLQGKLSE LQVEQTSLEP LQESPRPTGV WKSREVATEG IRGHRKMVLY TLRAPR (SEQ ID NO. 1).

The inventors have identified two novel regions of the NT-proBNP, comprising a part or all of the following amino acid residues:
SAS DLETSGLQEQ RNHLQGKLSE LQV (SEQ ID NO. 2, Peptide 1, amino acid residues 8-33 of SEQ ID NO. 1), and
IRGHRKMVLY TLRA (SEQ ID NO. 3, Peptide 2, amino acid residues 61-74 of SEQ ID NO. 1).

Accordingly, a first aspect of the present disclosure concerns a method for determining the concentration of N-terminal pro-brain natriuretic peptide (NT-proBNP) in a sample, said method comprising the following steps:
contacting the sample with at least one antibody which specifically binds to NT-proBNP within the amino acid sequence of SEQ ID NO. 2; and/or
contacting the sample with at least one antibody which specifically binds to NT-proBNP within the amino acid sequence of SEQ ID NO. 3;
wherein said at least one antibody is immobilized to a particle; and
determining a change in reflectance, scattering or transmittance of the sample wherein said change is indicative of the concentration of NT-proBNP in the sample.

According to one embodiment of said first aspect, said at least one antibody specifically binds to NT-proBNP within the amino acid sequence of SEQ ID NO. 2.

According to another embodiment of said first aspect, said at least one antibody comprises a polyclonal antibody and/or a mixture of monoclonal antibodies.

As used herein, the term "antibody" refers to polyclonal antibodies, a mixture of monoclonal antibodies of any isotype (IgA, IgG, IgD, IgM, IgY) or an antigen-binding fragment thereof, including but not limited to F(ab), F(ab'), F(ab')2, Fv fragments, single chain antibodies such as scFv, chimeric antibodies, humanized antibodies and a Fab expression library.

According to another embodiment of the above aspect and embodiments thereof, the polyclonal antibody and/or mixture of monoclonal antibodies binds with substantially same affinity to both glycosylated and non-glycosylated forms of NT-proBNP or fragments thereof. Said glycosylated and non-glycosylated forms of NT-proBNP or fragments thereof can be glycosylated and non-glycosylated recombinant NT-proBNP or fragments thereof, or glycosylated and non-glycosylated native NT-proBNP or fragments thereof.

According to another embodiment of the above aspect and embodiments thereof, said polyclonal antibody and/or the mixture of monoclonal antibodies binds/bind specifically to NT-proBNP with a $K_D$ of less than 10.0E-09 M, preferably less than 5.0E-09 M, more preferably less than 2.0E-09 M. Preferably, the polyclonal antibody and/or the mixture of monoclonal antibodies binds to recombinant NT-proBNP or fragments thereof with a $K_D$ of less than 10.0E-09 M, preferably less than 5.0E-09 M, more preferably less than 2.0E-09 M.

According to another embodiment of the above aspect and embodiments thereof, said polyclonal antibody and/or mixture of monoclonal antibodies binds specifically to the peptide of SEQ ID NO. 2 or a fragment thereof with a $K_D$ of less than 5.0E-09 M, preferably less than 2.0E-09 M.

According to an embodiment of the above aspect and embodiments thereof, said polyclonal antibody and/or mixture of monoclonal antibodies binds specifically to the peptide of SEQ ID NO. 3 or a fragment thereof with a $K_D$ of less than 10.0E-09 M, preferably less than 5.0E-09 M, more preferably less than 2.0E-09 M.

According to another embodiment of the above aspect and embodiments thereof, said at least one antibody is a polyclonal antibody or a mixture of monoclonal antibodies, preferably a polyclonal antibody, binding to at least one epitope chosen from the epitopes consisting of the amino acid sequences of SEQ. ID. NO. 4, SEQ. ID. NO 5, SEQ. ID. NO. 6, SEQ. ID. NO. 7, SEQ. ID. NO. 8, SEQ. ID. NO. 9 and SEQ. ID. NO. 10.

In one embodiment, said at least one antibody binds to one epitope having a sequence selected from the group consisting of SEQ. ID. NO. 4, SEQ. ID. NO 5, SEQ. ID. NO. 6, SEQ. ID. NO. 7, SEQ. ID. NO. 8, SEQ. ID. NO. 9 and SEQ. ID. NO. 10. In another embodiment, said at least one antibody binds to 2, 3, 4, 5 or more epitopes, wherein the epitopes are selected from the group consisting of SEQ. ID. NO. 4, SEQ. ID. NO 5, SEQ. ID. NO. 6, SEQ. ID. NO. 7, SEQ. ID. NO. 8, SEQ. ID. NO. 9 and SEQ. ID. NO. 10.

As used herein, the term "sample" refers to a sample of whole blood, blood plasma or blood serum obtained from a subject.

As used herein, the term "subject" refers to a mammal, preferably a human.

In a method according the first aspect and any embodiment thereof, the at least one antibody is immobilized to a particle. In one embodiment, the particle has an average (mean) size in the range of 150-300 nm, preferably 150-240 nm, more preferably 160-240 nm, and most preferably 180-220 nm, in uncoated form. The average size of the particle may be determined using various methods that are known in the art. One exemplary method of determining the average size of the particle is by using by using nanoparticle tracking analysis, for example by using the NanoSight® NS300 instrument (Malvern Panalytical). Nanoparticle tracking analysis (NTA) is based on the NanoSight®-principle and is a method for visualizing and analyzing particles in liquids that relates the rate of Brownian motion to particle size.

As used herein, the term "coating ratio" refers to the weight ratio of antibodies and particles in the coating process. For example, a coating ratio of e.g. 10% corresponds to the addition of 1 mg antibodies to a coating reaction with 10 mg latex particles (1:10).

According to one embodiment of the invention, the at least one antibody is coated onto the particle at a coating ratio (weight of antibodies: weight of latex particles) of at least 6%, (0.6:10) to 60% (6:10), preferably 6% (0.6:10)—30% (3:10), most preferably 10% (1:10)—20% (2:10).

In one embodiment, the particle is a latex particle, preferably a chloromethyl latex particle.

According to another embodiment of the first aspect, and any embodiments thereof, the change in reflectance, scattering or transmittance is determined at a wavelength in the range from 350 to 700 nm, preferably at about 450-550 nm, such as 546 or 548 nm.

According to another embodiment of the first aspect, and freely combinable with any embodiments thereof, the method includes a step of calibration using a calibrator. As used herein, the term "calibrator" refers to a substance of known concentration, wherein said calibrator is chosen from a peptide with the amino acid sequence of SEQ ID NO. 2, or a fragment thereof; or a peptide with the amino acid sequence of SEQ ID NO. 3, or a fragment thereof. In one embodiment, the calibrator has the amino acid sequence of any one of SEQ. ID. NO. 4, SEQ. ID. NO 5, SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, or combinations thereof. In another embodiment, a native or full-length NT-proBNP according to SEQ ID NO. 1 is used as calibrator. In one embodiment the calibrator is glycosylated. In another embodiment, the calibrator is non-glycosylated.

According to preferred embodiment of the first aspect, and freely combinable with any embodiments thereof, the change in reflectance, scattering or transmittance of the sample is a change in transmittance, and the method is performed as a turbidimetric measurement of the concentration of NT-proBNP.

According to another embodiment the change in reflectance, scattering or transmittance of the sample is a change in reflectance or scattering, and the method is performed as a nephelometric measurement of the concentration of NT-proBNP.

A second aspect of the present disclosure relates to an immunoparticle comprising a particle as the core coated with at least one antibody chosen from a polyclonal antibody or a mixture of monoclonal antibodies which specifically binds to NT-proBNP within the amino acid sequence of SEQ ID NO. 2; or which specifically binds to NT-proBNP within the amino acid sequence of SEQ ID NO. 3, preferably wherein said at least one antibody specifically binds to NT-proBNP within the amino acid sequence of SEQ ID NO. 2.

According to an embodiment of said second aspect, said polyclonal antibody and/or mixture of monoclonal antibodies binds with substantially same affinity to both glycosylated and non-glycosylated forms of NT-proBNP. Said glycosylated and non-glycosylated forms of NT-proBNP can be glycosylated and non-glycosylated recombinant NT-proBNP or fragments thereof or glycosylated and non-glycosylated native NT-proBNP or fragments thereof.

Preferably said polyclonal antibody and/or the mixture of monoclonal antibodies binds specifically to NT-proBNP and exhibits a $K_D$ to recombinant NT-proBNP of less than 10.0E-09 M, such as less than 5.0E-09 M, preferably less than 2.0E-09 M.

According to an embodiment, the polyclonal antibody and/or the mixture of monoclonal antibodies binds/bind specifically to the peptide of SEQ ID NO. 2 with a $K_D$ of less than 5.0E-09 M, preferably less than 2.0E-09 M.

According to another embodiment, the polyclonal antibody and/or the mixture of monoclonal antibodies binds/bind specifically to the peptide of SEQ ID NO. 3 with a $K_D$ of less than 10.0E-09 M, preferably less than 5.0E-09 M, more preferably less than 2.0E-09 M.

According to an embodiment of said second aspect, said at least one antibody is a polyclonal antibody or a mixture of monoclonal antibodies, preferably a polyclonal antibody, binding to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9, and/or SEQ. ID. NO. 10.

According to an embodiment of said second aspect, freely combinable with all aspects and embodiments herein, said core is a latex core having an average size in the range of 150-300 nm, preferably about 150-240 nm, more preferably 160-240 nm, most preferably 180-220 nm in uncoated form, determined by using nanoparticle tracking analysis, for example by using the NanoSight® NS300 instrument (Malvern Panalytical). Nanoparticle tracking analysis (NTA) is based on the NanoSight®-principle and is a method for visualizing and analyzing particles in liquids that relates the rate of Brownian motion to particle size.

A third aspect of the disclosure relates to a kit for particle enhanced optical determination of a concentration of NT-proBNP in a sample, said kit comprising:
at least one antibody which specifically recognizes and binds to NT-proBNP within the amino acid sequence of SEQ ID NO. 2 or within SEQ ID NO. 3, wherein said at least one antibody is immobilized to a particle;
a calibrator, and optionally,
instructions for using the kit to determine the concentration of NT-proBNP in the sample.

According to an embodiment of said third aspect, the at least one antibody immobilized to a particle forms an immunoparticle according to the second aspect and any embodiment thereof.

According to an embodiment, the kit includes a mixture of immunoparticles wherein said mixture comprises both immunoparticles coated at least one antibody which binds to NT-proBNP within the amino acid sequence of SEQ ID NO. 2, and immunoparticles coated with at least one antibody which binds to NT-proBNP within the amino acid sequence of SEQ ID NO. 3.

According to an embodiment of said third aspect, the kit comprises a storage buffer in which the immunoparticles are suspended. In a preferred embodiment, said storage buffer comprises a density gradient medium wherein the density of said storage buffer is adjusted to substantially the same specific weight as the specific weight of the immunoparticles.

According to another embodiment of said third aspect, the kit further comprises an assay buffer. In one embodiment, said assay buffer comprises an accelerator, a blocking agent, or a combination of both.

In one preferred embodiment, the accelerator is polyethylene glycol (PEG). In a more preferred embodiment, PEG is present in a concentration of 0.05-0.5% (wt/vol), preferably 0.05-0.4% (wt/vol).

According to another embodiment, the blocking agent to avoid or reduce non-specific interactions during the immunoreaction, and thereby improve the accuracy of the immunoassay. In one embodiment, the blocking agent comprises a protein (e.g. from a bovine species, rabbit, or chicken) preferably at a concentration of 0.001-2%. According to one embodiment the blocking agent is IgG in a concentration of about 0.1%.

According to another embodiment, said particle enhanced optical method is chosen from nephelometry and turbidimetry, preferably turbidimetry, and the instructions for using the kit define the steps of performing a turbidimetric or nephelometric analysis.

A fourth aspect of the disclosure relates to a method for identifying a subject with heart failure or having an elevated risk for heart failure by determining the concentration of NT-proBNP in a bodily fluid sample of said subject, said method comprising:

provided an immunoparticle according to the second aspect or any embodiments thereof;

reacting the sample with said immunoparticles;

detecting a change in reflectance, scattering or transmittance of the sample, wherein said change in reflectance, scattering or transmittance of the sample is indicative for the amount of NT-proBNP;

wherein said change in reflectance, scattering or transmittance is indicative that the subject has heart failure or an elevated risk for heart failure.

According to one embodiment, the method further comprises the step of determining the elevated concentration of NT-proBNP above a pre-determined concentration. The pre-determined concentration is an age- and sex-dependent concentration of NT-proBNP, and known in the art.

According to one embodiment, heart failure is congestive heart failure, for example congestive heart failure of New York Heart Association (NYHA) Functional Classification classes II, III, or IV (Dolgin M, Association NYH, Fox AC, Gorlin R, Levin R I, New York Heart Association. Criteria Committee. Nomenclature and criteria for diagnosis of diseases of the heart and great vessels. 9th ed. Boston, Mass.: Lippincott Williams and Wilkins; Mar. 1, 1994).

In the above, the sample is a sample chosen from blood plasma and blood serum and the change in reflectance, scattering or transmittance is a change in transmittance and the method is a turbidimetric method.

In the alternative, the sample is a sample chosen from blood plasma and blood serum and the change in reflectance, scattering or transmittance is a change in reflectance or scattering and the method is a nephelometric method.

A fifth aspect of the disclosure relates to a polyclonal antibody or a mixture of monoclonal antibodies, binding specifically to NT-proBNP within the amino acid sequence of SEQ ID NO.2, or SEQ ID NO.3. In one embodiment of the invention, the polyclonal antibody or a mixture of monoclonal antibodies exhibits a disassociation constant, $K_D$, to NT-proBNP of less than 10.0E-09 M, preferably less than 5.0E-09 M, and most preferably less than 2.0E-09 M. The disassociation constant can be determined using surface plasmon resonance (SPR) technology in a method often referred to as the Biacore™ method, well-known to a person skilled in the art.

Preferably said polyclonal antibody or mixture of monoclonal antibodies, is capable of specifically recognizing and binding to both glycosylated and non-glycosylated forms of recombinant NT-proBNP or fragments thereof with substantially same affinity.

According to another embodiment of said fifth aspect, said polyclonal antibody or mixture of monoclonal antibodies is preferably capable of specifically recognizing an epitope of NT-proBNP within the amino acid sequence of SEQ ID NO. 2, and/or an epitope of NT-proBNP within the amino acid sequence of SEQ ID NO. 3.

Preferably said polyclonal antibody or mixture of monoclonal antibodies binds to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9 and/or SEQ. ID. NO. 10.

Another aspect of the present disclosure is the use in vitro of a polyclonal antibody or mixture of monoclonal antibodies of the invention in diagnosis, monitoring, stratifying or predicting mortality rate in patients with heart failure, in particular congestive heart failure or patients at risk of developing heart failure, in particular congestive heart failure.

In the above aspect, said polyclonal antibody preferably binds to NT-proBNP or a fragment thereof within the amino acid sequence of SEQ ID NO. 2 or a fragment thereof, and/or the amino acid sequence of SEQ ID NO. 3 or a fragment thereof. In one embodiment, said polyclonal antibody binds to a peptide with the amino acid sequence of SEQ ID NO:2 or SEQ ID NO:3. In another embodiment, said polyclonal antibody binds to a peptide with the amino acid sequence of SEQ ID NO:2 and SEQ ID NO:3.

According to an embodiment of this aspect, said polyclonal antibody or mixture of monoclonal antibodies, preferably polyclonal antibody, binds to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9 and/or SEQ. ID. NO. 10.

Yet another aspect of the present disclosure is the in vitro use of a peptide of SEQ ID NO. 2; or a peptide of SEQ ID NO. 3, or fragments thereof, or a combination thereof, in a method for determining the concentration of NT-proBNP in a sample, preferably for turbidimetrically determining the concentration of NT-proBNP in a sample.

The foregoing summary is illustrative only and is not intended to be in any way limiting. In addition to the illustrative aspects, embodiments and features described above, further aspects, embodiments and features will become apparent by reference to the following drawings and the detailed description and examples.

BRIEF DESCRIPTION OF THE DRAWINGS

The invention is now described, by way of example, with reference to the accompanying drawings, in which.

ProBNP is formed following the translation and cleavage of the signal peptide of pre-proBNP molecule. It is then glycosylated at several sites. Two pools of proBNP that are different in the status of T71 glycosylation are formed: non-glycosylated at T71 and molecules glycosylated at this site. Glycosylation suppresses the subsequent processing of proBNP. Only proBNP that is not glycosylated at T71 can be effectively processed into BNP and NT-proBNP. Non-processed proBNP, NT-proBNP and BNP are released into the blood.

Figures 1, 2:
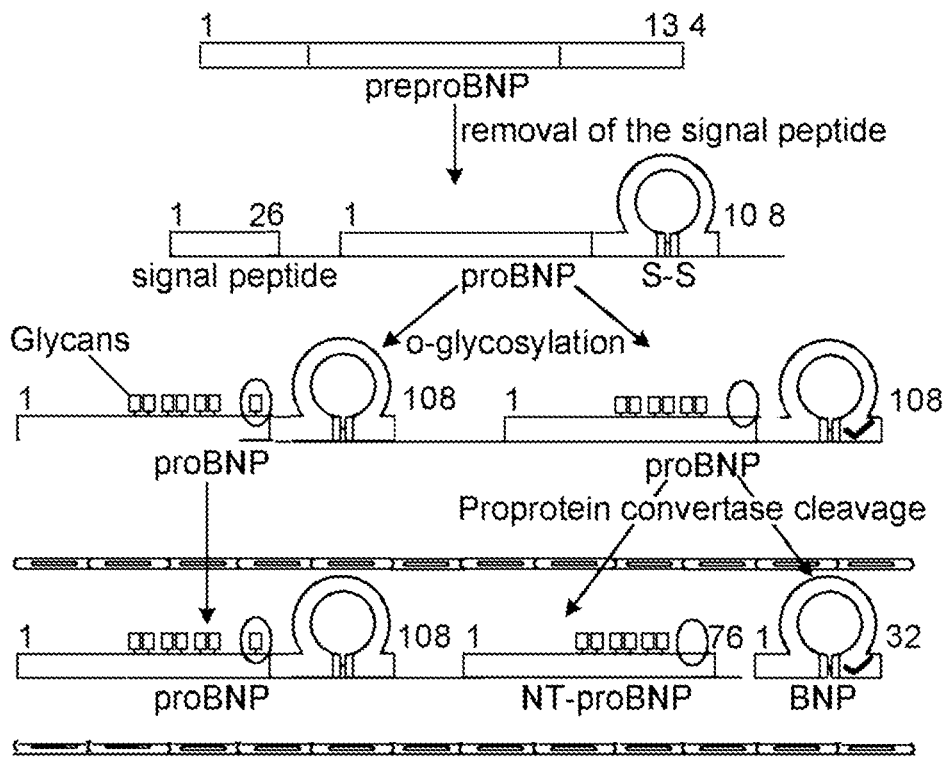
FIG. 1 shows the scheme of proBNP processing (Source: TechNotes I Human ProBNP, BNP and NT-proBNP, HyTest Ltd., January 2019, downloaded 07.08.2019).

FIG. 2 presents the amino acid sequence of NT-proBNP as amino acids 27-102 of NCBI Reference Sequence NP_002512, with the two peptides identified by the present inventors indicated: amino acid position 8-33 (Peptide 1) and 61-74 (Peptide 2).

Figure 3:
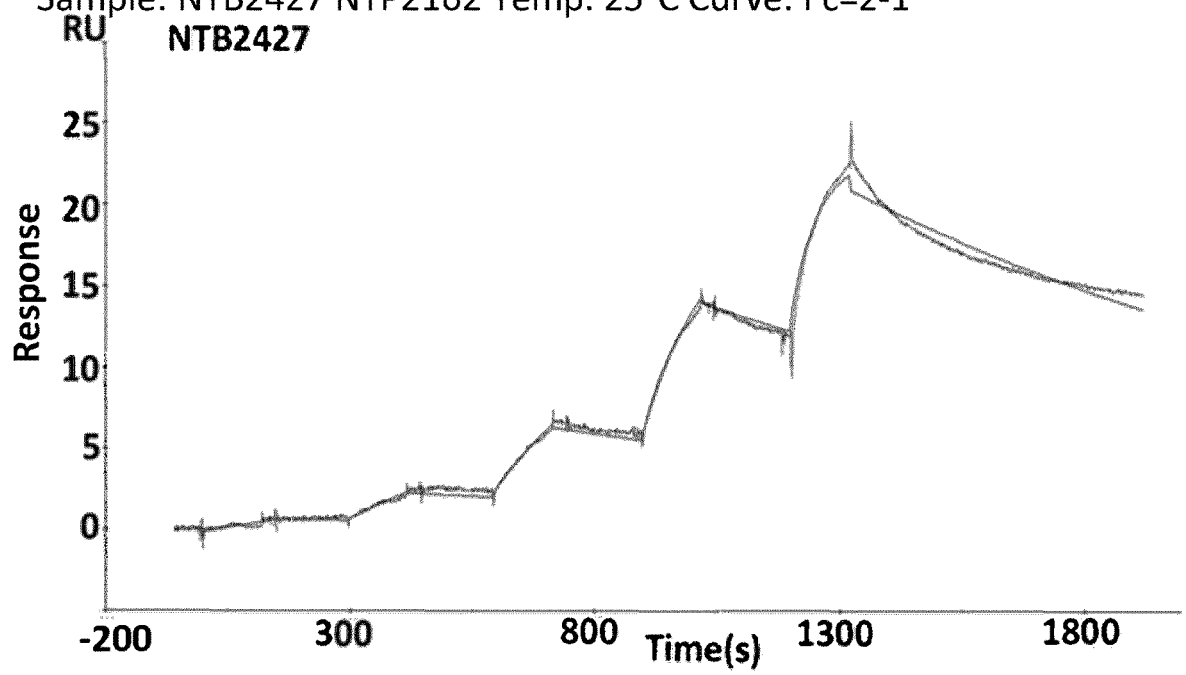

FIG. 3 shows an example of the Biacore™ affinity analysis for IgG antibody from rabbit antiserum, purified against non-glycosylated recombinant NT-proBNP, and tested against a Biacore™ chip with full-length antigen. Equilibrium dissociation constant $K_D$=1.35E-09 M.

Figure 4:
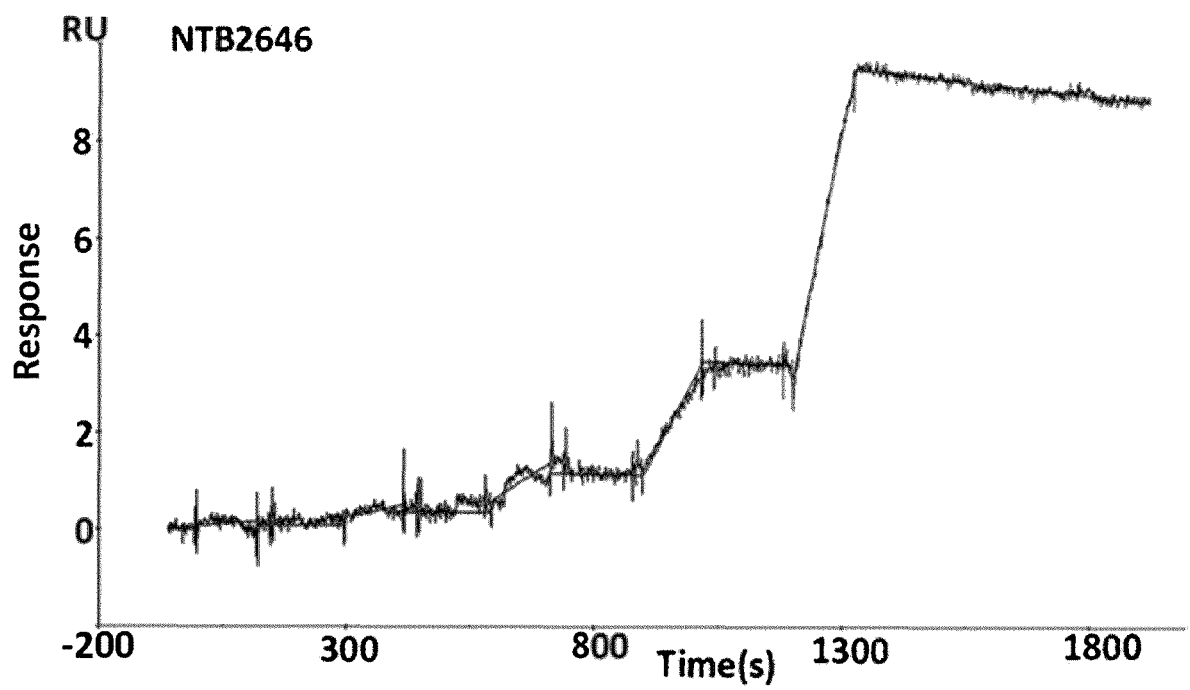

FIG. 4 shows the Biacore™ affinity results for IgY antibody purified against Peptide 1 and tested against a Biacore™ chip with full-length antigen. Equilibrium dissociation constant $K_D$=2.11E-09 M.

Figure 5:
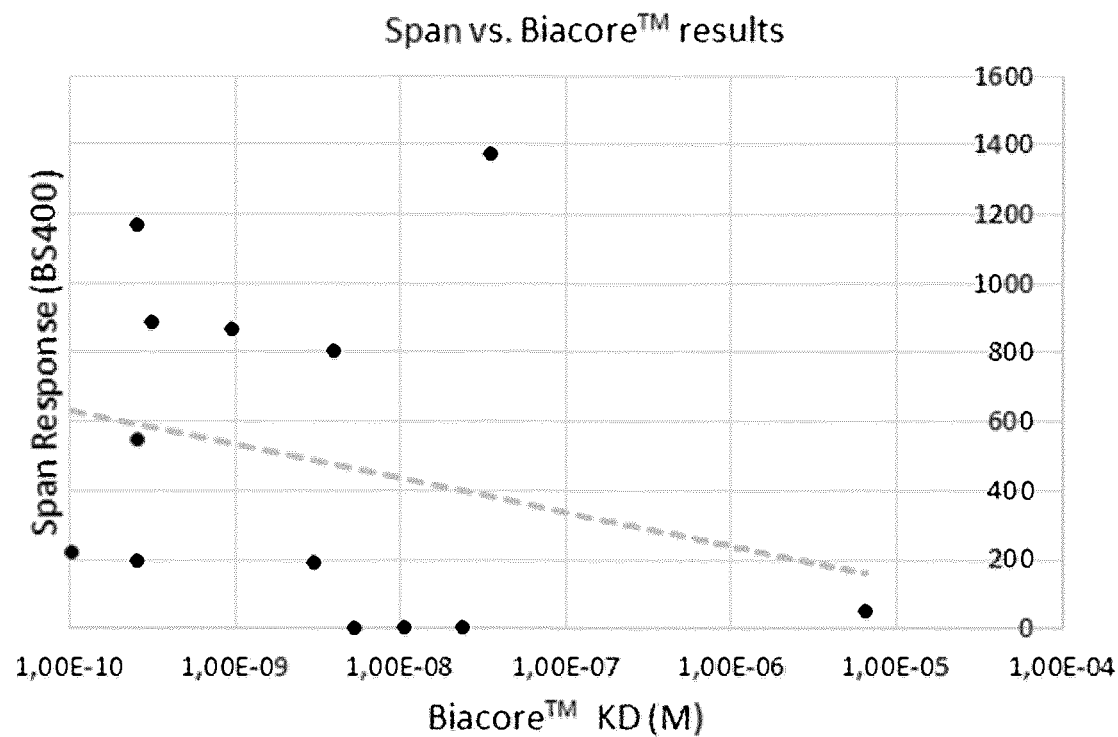

FIG. 5 shows the correlation between the Biacore™ affinity constant ($K_D$) and the span response readout achieved with a clinical chemistry analyser (Mindray® BS-400).

Figure 6:
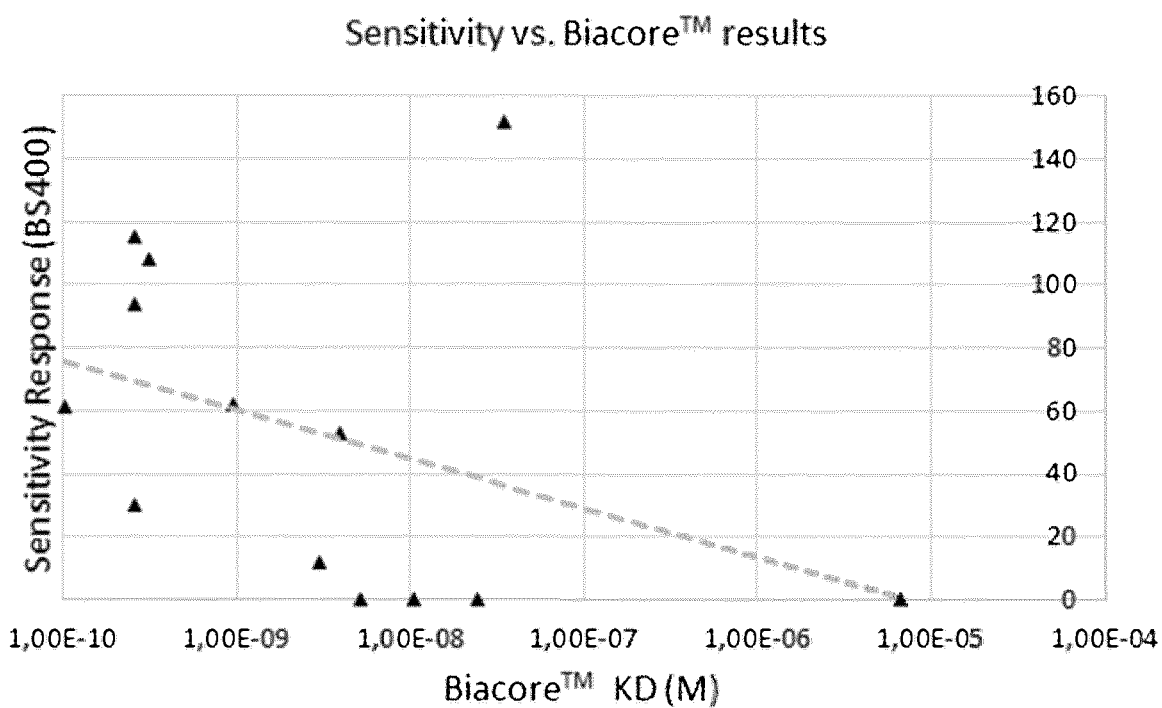

FIG. 6 shows the correlation between the Biacore™ affinity constant ($K_D$) and the sensitivity achieved with a clinical chemistry analyser (Mindray® BS-400).

Figure 7:
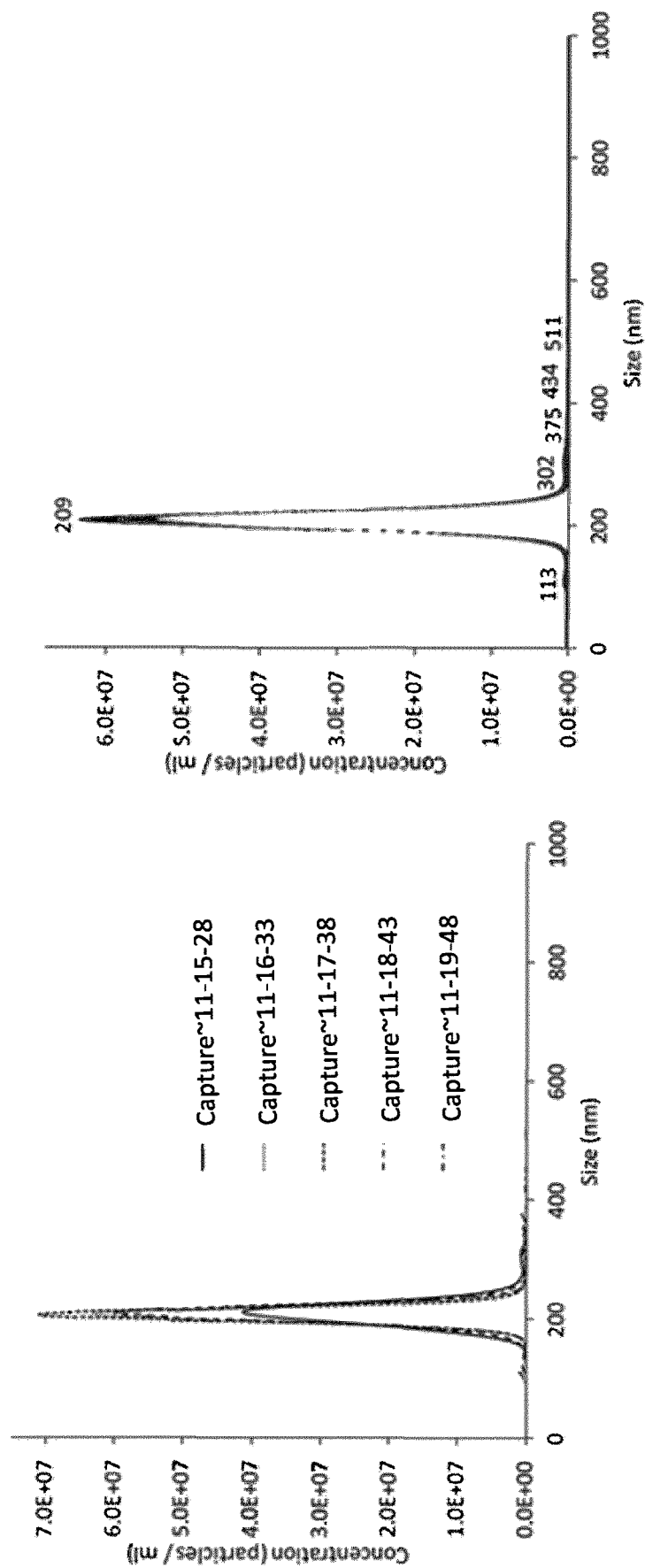

FIG. 7 shows the size distribution of immunoparticles determined using a NanoSight® NS300 instrument (Malvern Panalytical Ltd., Malvern, UK), the results confirming that a substantially homogenous lot was achieved. An immunoparticle lot made with 200 nm latex particles and a 10% coating ratio was used for the measurement.

Figure 8:
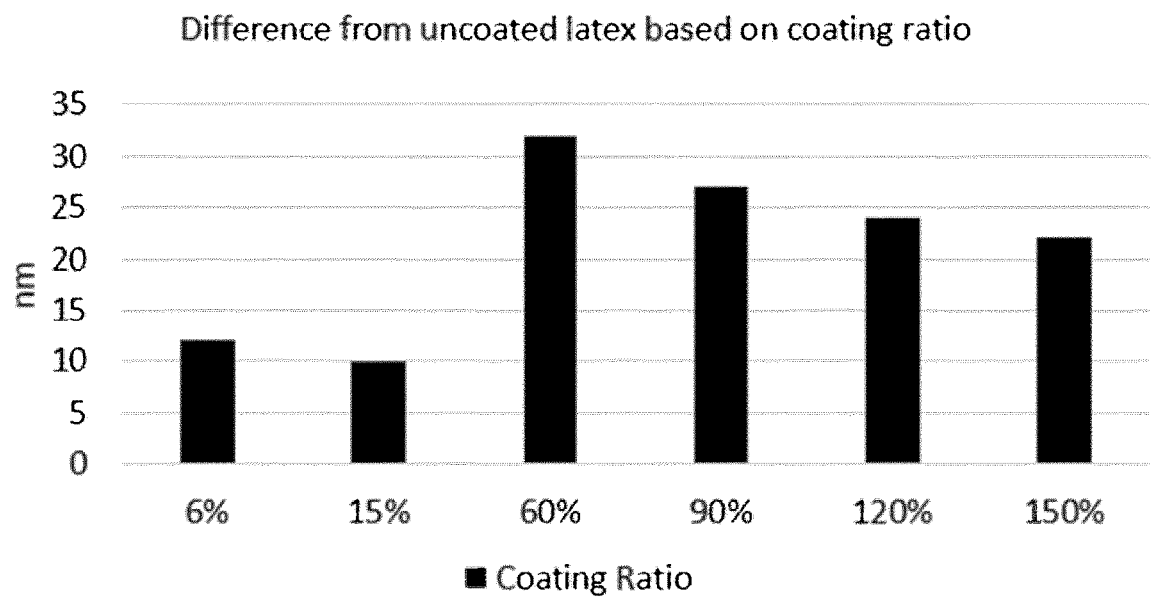

FIG. 8 shows the difference in particle size (nm, mean) compared to uncoated latex particles based on coating ratio. The measurements were performed on a NanoSight® NS300 instrument (Malvern Panalytical Ltd., Malvern, UK).

Figure 9:
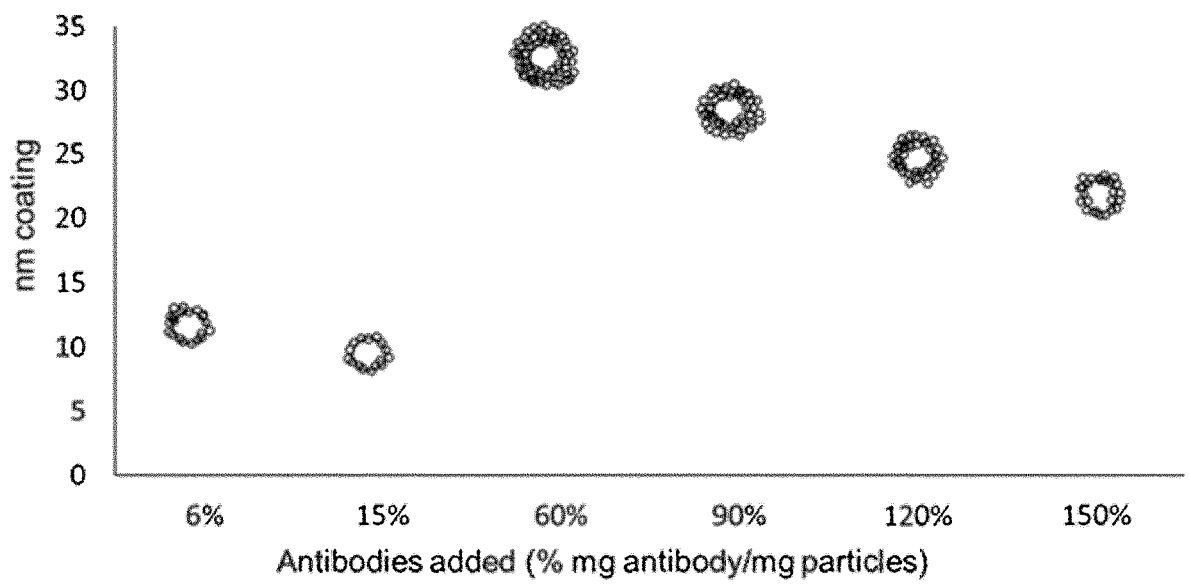

FIG. 9 schematically illustrates the estimated structure of an immunoparticle carrying an overload of antibodies, based on particle size measurements. A mean particle size (diameter) increase of about 20 nm indicates that one layer of antibodies is present, whereas an increase of about 40 or about 60 nm indicates two or three layers, respectively.

Figure 10:
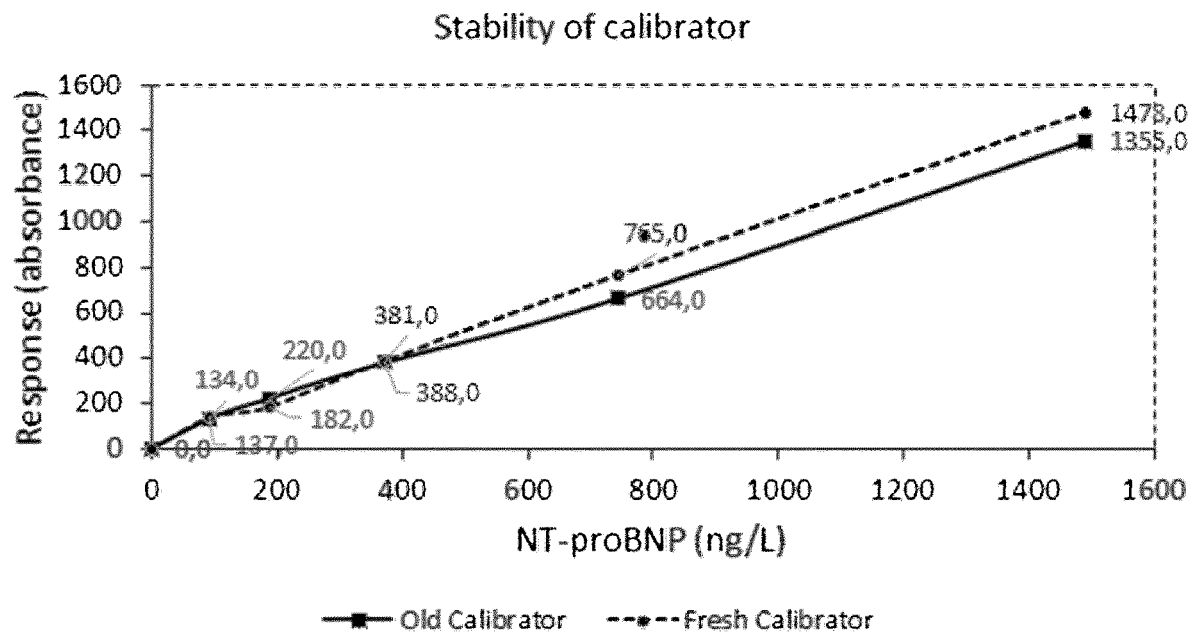

FIG. 10 shows two calibration curves for 200 nm particles coated with antibodies at a coating ratio of 50% using two different sets of calibrators, one fresh and one stored for 2 months at 4° C., confirming the stability of the antigen in the buffer.

Figure 11:
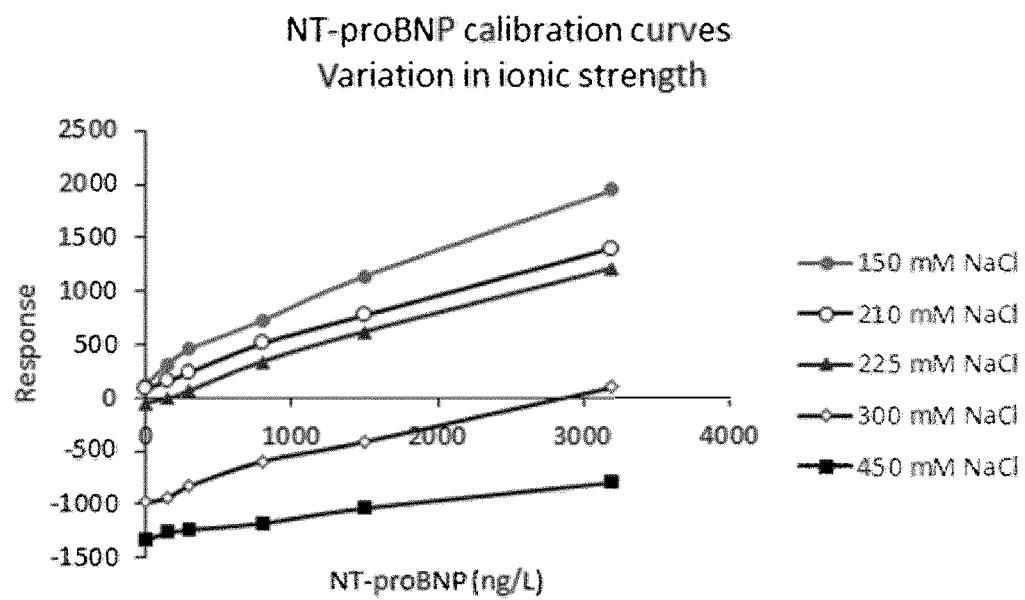

FIG. 11 illustrates how the calibration curve can be fine-tuned by varying the ionic strength in the assay buffer.

Figure 12:
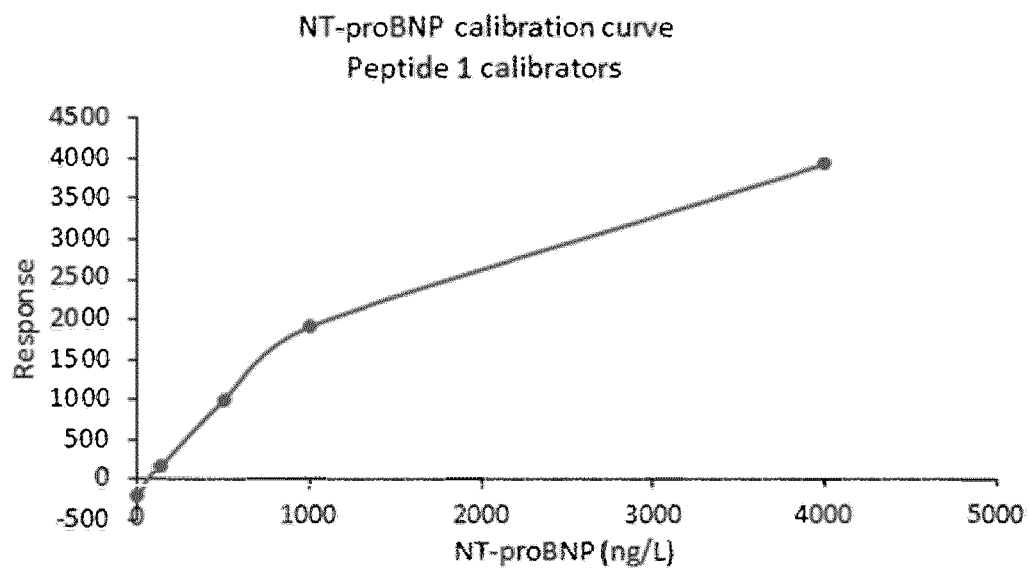

FIG. 12 shows an example of a calibration curve for lot 46 (200 nm particles coated with antibodies raised against the peptide of SEQ ID NO. 2 (Peptide 1)), using the same peptide (SEQ ID. 2) as calibrator antigen.

Figure 13:
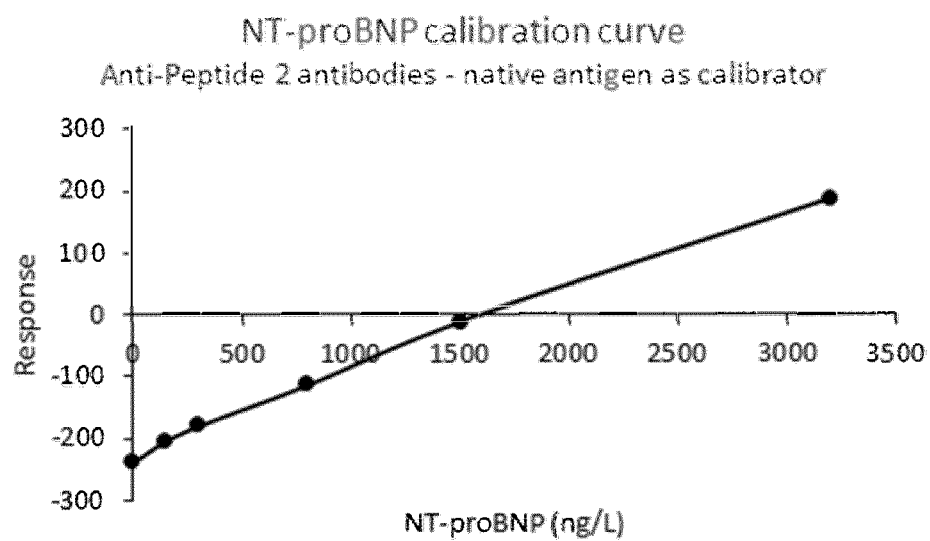

FIG. 13 shows an example of a calibration curve for lot 49 (200 nm particles coated with antibodies raised towards the peptide of SEQ ID NO 3 (Peptide 2)), using native antigen as calibrator antigen.

Figure 14:
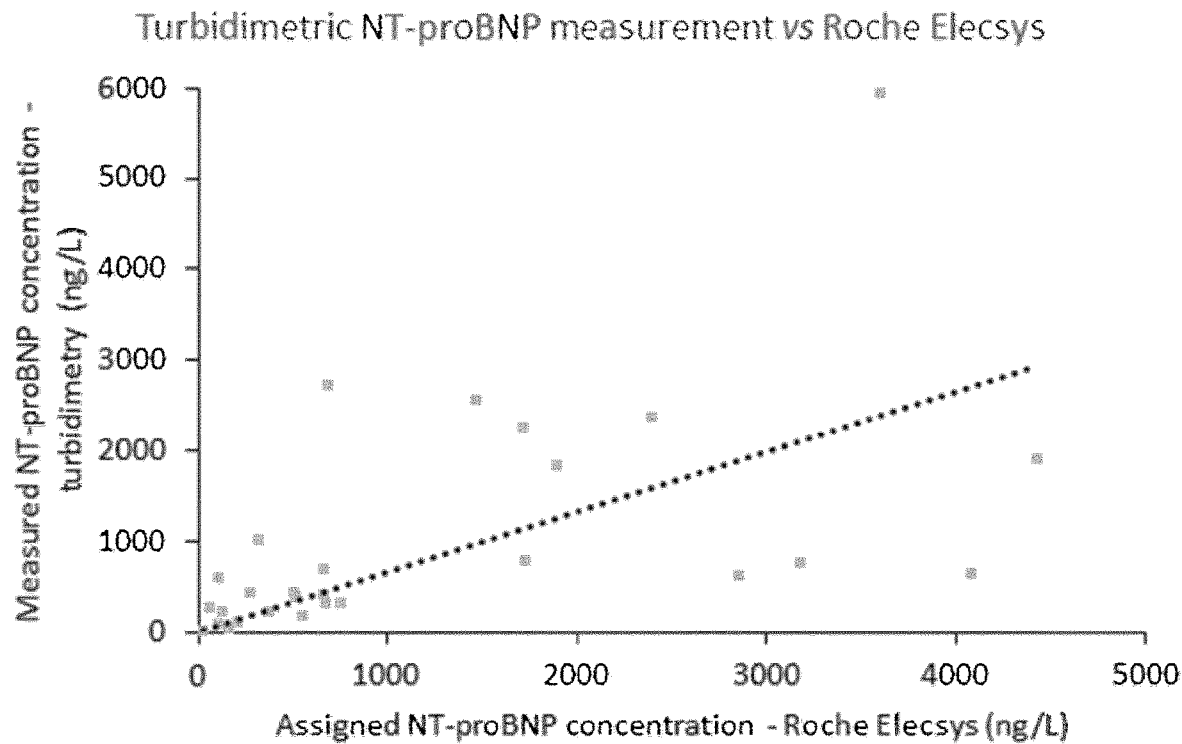

FIG. 14 is a graph comparing the results (ng/l) of 28 turbidimetric measurements of NT-proBNP to the assigned values of the same patient samples measured using the Roche Elecsys® assay.

Figure 15:
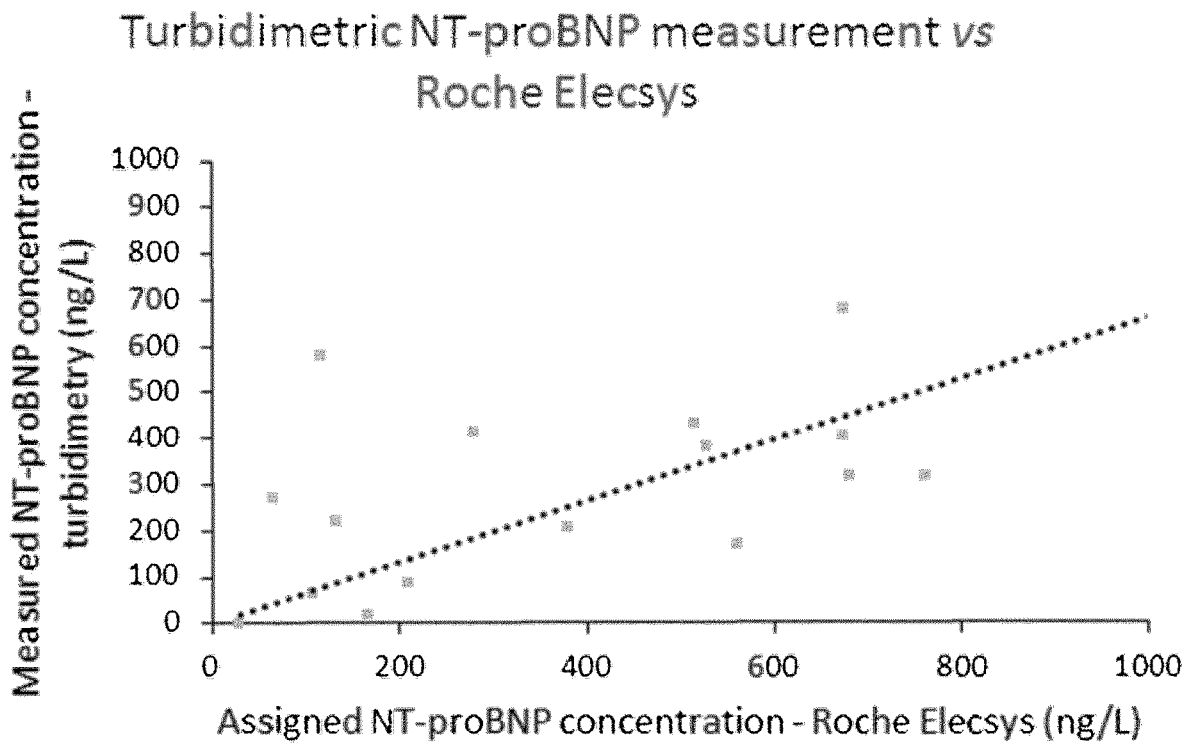

FIG. 15 shows the same data as FIG. 14, here only including samples with a measured NT-proBNP concentration lower than 1000 ng/L.

Figure 16:
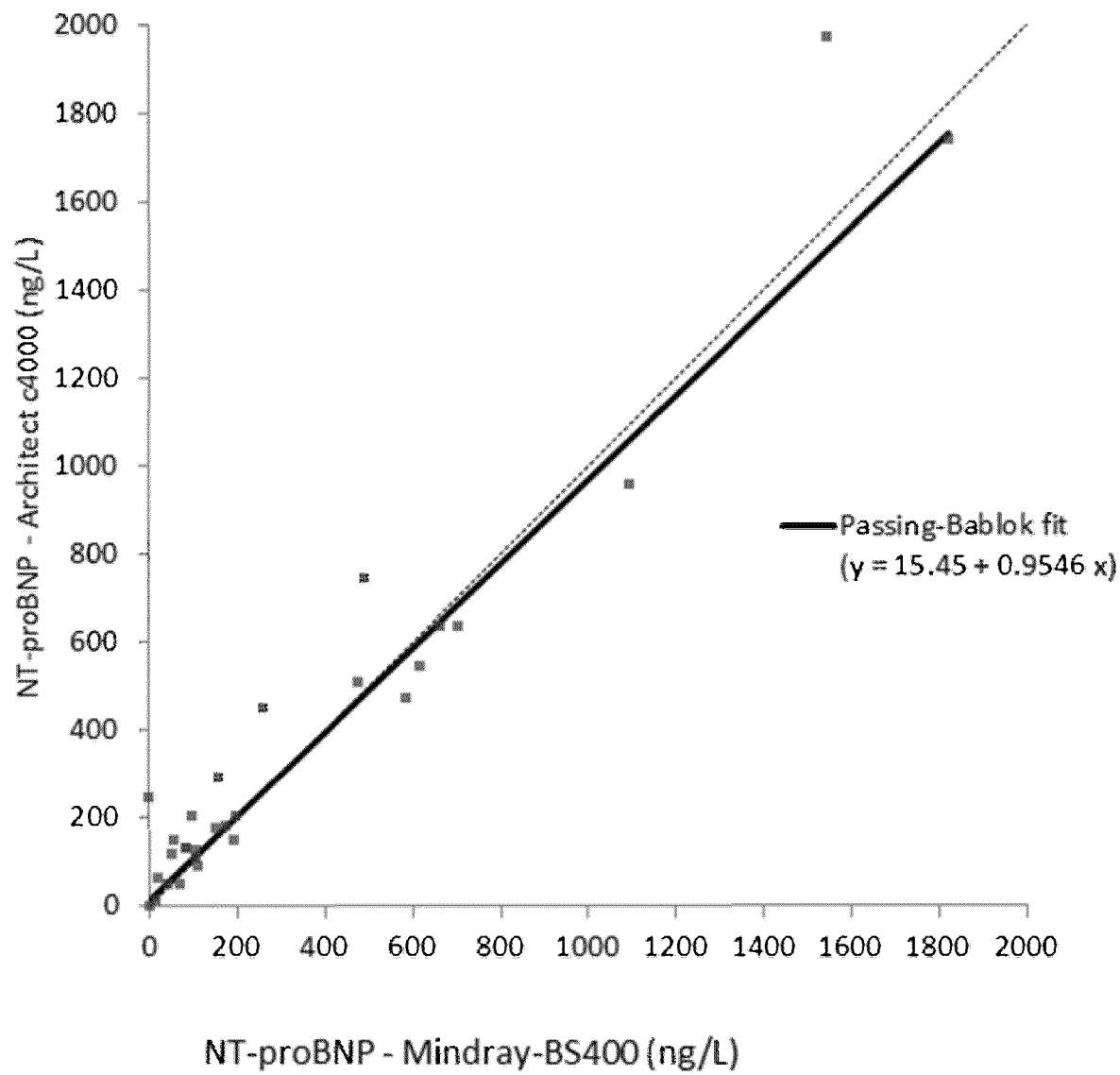

FIG. 16 is a graph showing the correlation between 29 patient samples measured on two different instruments, Mindray® BS-400 and Architect c4000, using the same reagents and calibrators on both instruments.

Figure 17:
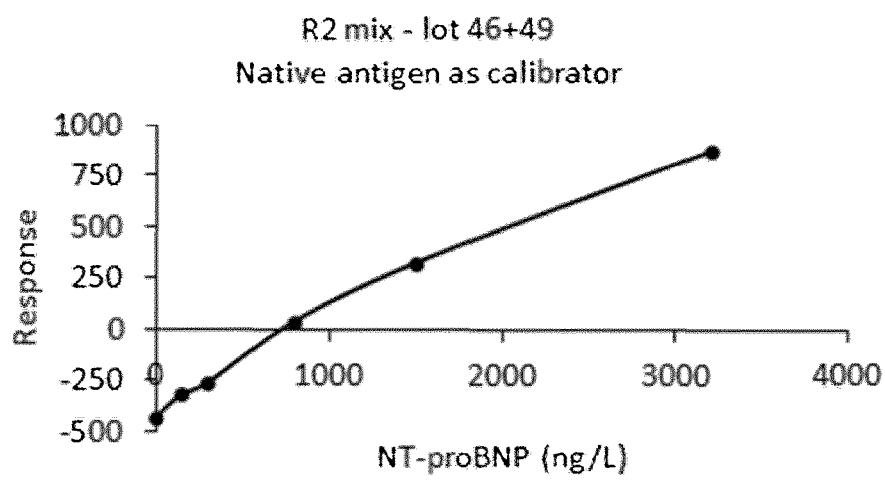

FIG. 17 is a graph where the response from an assay using a mixture of immunoparticles is plotted against the concentration of NT-proBNP.

Figure 18:
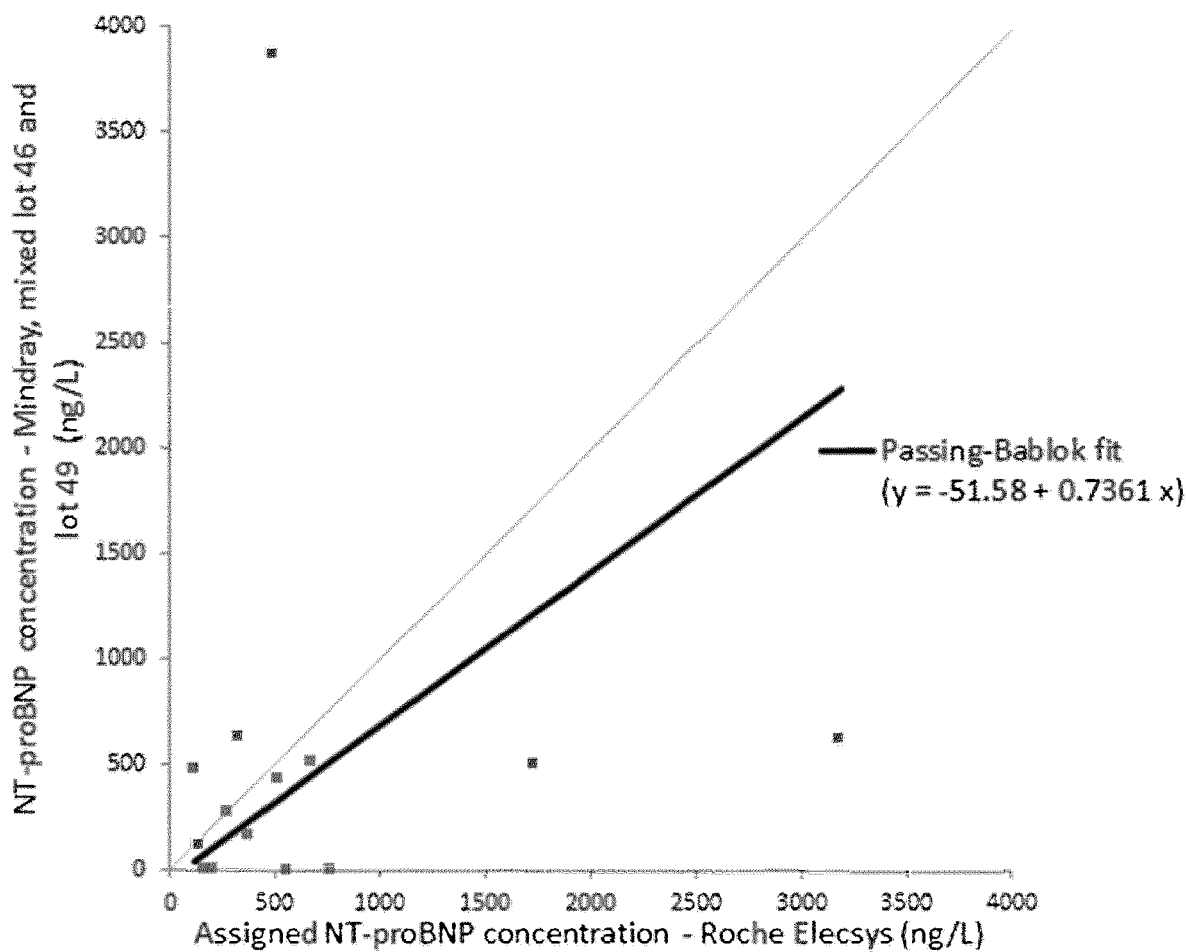

FIG. 18 is a graph comparing the results (ng/l) of 14 turbidimetric measurements using a mixture of immunoparticles against NT-proBNP to the assigned values of the same patient samples measured using the Roche Elecsys® assay.

DETAILED DESCRIPTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

The term "sample" as in "a sample of whole blood" refers to a sample taken from a human or animal body, and which sample will not be returned to said human or animal body. There are standardized methods for obtaining and handling a blood sample taken from a human or animal body, involving the use of needles, syringes, micro cuvettes etc. These methods are well-known to persons skilled in the art. The currently most preferred type of sample is lithium heparin treated sample of whole blood. There are several blood collection tubes containing spray coated lithium heparin readily available from various commercial supplies, e.g. the BD Vacutainer® available from BD, Oakville, Ontario, Canada.

The term "immunogen" in this disclosure refers to substance used to produce antibodies and includes conjugated and unconjugated forms.

The term "specifically binds to NT-proBNP within the amino acid sequence of SEQ ID NO. 2 or SEQ ID NO. 3" is understood to mean that only amino acids within this amino acid stretch (SEQ ID NO. 2 or SEQ ID NO. 3) of NT-proBNP are responsible for specifically recognizing and/or binding to the antibody. In other words, an antibody as described herein specifically recognizes and/or binds to an epitope within this amino acid stretch (SEQ ID NO. 2 or SEQ ID NO. 3) of NT-proBNP.

The term "specifically recognizes an epitope" or "specifically binds an epitope" is understood to mean that only the amino acids of the epitope are responsible for the binding to the antibody. Accordingly, the term "epitope" denotes the antigenic determinant, namely a specific part or parts of an antigen such as NT-proBNP to which an antibody binds (such as an epitope comprising part or all amino acids found in the amino acid sequences corresponding to SEQ ID NO: 2 or 3). None of the other amino acids of an antigen such as NT-pro-BNP are supposed to be involved in the binding of the antibody. Lack of cross-reactivity of an antibody to other molecules means that the antibody has high epitope specificity.

Further, "binding with substantially the same affinity" is understood to mean that an antibody binds for example to two or more different peptides with binding affinities in the same order of magnitude. The antibody or antibodies as described herein bind to a peptide, e.g. an 8-mer peptide of in the context of an epitope mapping assay, or to a protein, with an affinity of at least about 50%, of at least about 60%, of at least about 70%, of at least about 80%, of at least about 90%, of at least about 95%, of at least about 97%, of at least about 98%, or of at least about 99% of the affinity of the same antibody or antibodies binding to another peptide or protein.

In another embodiment, an anti-NT-proBNP antibody or antigen-binding fragment thereof which binds to non-glycosylated NT-proBNP with the same or substantially the same affinity as to a glycosylated form of NT-proBNP, e.g. native NT-proBNP.

As used herein, the term "at least one antibody or antibodies" refers to polyclonal antibodies, a mixture of monoclonal antibodies of any isotype (IgA, IgG, IgD, IgM, IgY) or an antigen-binding fragment thereof, including but not limited to F(ab), F(ab'), F(ab')2, Fv fragments, single chain antibodies such as scFv, chimeric antibodies, humanized antibodies and a Fab expression library The terms "binding fragment of an antibody" or "antibody fragment" refer to a fragment of a full-length antibody which results e.g. from deletion of N-terminal or C-terminal amino acids of the full-length antibody and which maintains the capacity to bind the cognate antigen with about the same specificity and/or $K_D$ as the full-length antibody.

Assays to determine binding specificity and $K_D$ of an antibody are well known and routinely practiced in the art. For a comprehensive discussion of such assays, see Harlow et al. (Eds.), Antibodies: A Laboratory Manual; Cold Spring Harbor Laboratory; Cold Spring Harbor, N.Y. (1988), Chapter 6.

One approach to measure specificity is by testing an antibody for binding to its cognate antigen and other non-related antigens using Western Blotting or ELISA. Another approach to measure affinity of binding of an antibody to its antigen is by surface plasmon resonance (SPR) using e.g. the Biacore™ assay platform and software (GE Healthcare).

Size of latex particles: For commercially available particles, the particle size is indicated by the manufacturer. For the purpose of this application, particle size is determined using nanoparticle tracking analysis or the NanoSight®-principle, for example using the NanoSight® NS300 instrument (Malvern Panalytical) which utilizes the properties of both light scattering and Brownian motion in order to obtain the size distribution and concentration measurement of particles in liquid suspension. In brief, a laser beam is passed through a sample chamber, containing the particles of interest, suspended in solution. The particles in the path of this beam scatter light in such a manner that they can be visualized via 20× magnification microscope onto which a camera is mounted. The camera operates at 30 frames per second (fps), capturing a video file of the particles moving under Brownian motion. The software tracks many particles individually and using the Stokes-Einstein equation calculates their hydrodynamic diameters. The measurement is controlled via Standard Operating Procedures. More information is available at the manufacturer's website (incorporated by reference).

Blood tests, involving laboratory examination of a sample of blood to obtain information about its physical and chemical properties, today form the foundation of medical diagnosis. Hundreds of haematological tests and procedures have been developed over the years. While the tests were originally performed manually, one by one, the field of clinical chemistry has become highly automated. Today multiple tests can be carried out simultaneously on one single sample of blood using automated clinical chemistry analysers, instruments frequently referred to as autoanalyzers.

While the presently disclosed assay method can be performed manually, the assay is preferably performed on an autoanalyzer, as this allows high throughput, reduces error and minimizes staffing requirements. A closed, automated sample handling also minimizes the risk that staff is exposed to possible blood borne pathogens.

When taking a blood sample, blood is usually drawn from a vein in the arm and collected in standardized sterile blood collection tubes. Different tubes are available, depending on which component or components that is to be analysed. A blood collection tube can be empty, or prefilled with a buffer or more frequently, with an anticoagulant. Examples of anticoagulants include sodium citrate, lithium-heparin, and EDTA. Different combinations are also possible, there are for example tubes containing sodium heparin and EDTA. The Vacutainer® (BD, Becton, Dickinson and Company) is one example of blood collection tubes, available in different sizes and pre-filled with various reagents.

A distinction is made between plasma samples and serum samples. When a plasma sample is desired, blood is collected in a tube containing an anticoagulant, the tube is turned upside down about 5 to 10 times directly after filling, in order to ensure mixing. The tubes are then stored in an upright position in room temperature to avoid haemolysis. EDTA and lithium heparin containing tubes can generally be stored up to 4 hours in room temperature. Alternatively, the tubes must be deep-frozen and stored for later analysis.

For obtaining a serum sample, blood is collected in an empty sample tube or a tube containing a coagulation activator. After filling, the tubes are turned upside down about 5 to 10 times directly after filling, in order to ensure mixing. The tubes are then stored in an upright position in room temperature to avoid haemolysis. In most cases, serum tubes can be stored in room temperature and without centrifuging for up to 4 hours. Upon arrival in the laboratory, the tubes are centrifuged, for example centrifuged for 10 minutes at 2000×g. Following centrifugation, a layer of blood cells can be seen at the bottom of the tube, and the fluid above is called serum. The serum should be separated and stored cold without any additives until transport or analysis.

A first aspect of the present description concerns a method for determining the concentration of N-terminal pro-brain natriuretic peptide (NT-proBNP) in a sample, said method comprising the following steps:
contacting the sample with at least one antibody which specifically binds to NT-proBNP within the amino acid sequence of SEQ ID NO. 2; and/or
contacting the sample with at least one antibody which specifically binds to NT-proBNP within the amino acid sequence of SEQ ID NO. 3;
wherein said at least one antibody is immobilized to a particle; and
determining a change in reflectance, scattering or transmittance of the sample wherein said change is indicative of the concentration of NT-proBNP in the sample.

According to a preferred embodiment of said first aspect, said at least one antibody specifically binds to NT-proBNP within the amino acid sequence of SEQ ID NO. 2.

The present inventors were surprised to see that an analyte such as NT-proBNP, which is present at very low concentrations, could be reliably detected in an immunoparticle-based assay using polyclonal antibodies raised against a peptide within the amino acid sequence of SEQ ID NO. 2; and/or a peptide within the amino acid sequence of SEQ ID NO. 3. This is very advantageous, because—when realized in the form of a turbidimetric or nephelometric assay, the determination of the concentration of NT-proBNP can be performed on any automated clinical analyser, and thus leads to higher throughput, shorter response times, and savings in labour and cost. Another advantage is that the use of a short peptide for raising the antibodies, and in the calibrator, reduces the cost of manufacturing the immunoparticles and the reagents, as peptide synthesis is rather costly.

According to an embodiment of said first aspect, the at least one antibody comprises a polyclonal antibody and/or a mixture of monoclonal antibodies. The use of a polyclonal antibody has an advantage in particle assisted assays, as a polyclonal antibody is capable of binding to several epitopes, resulting in higher overall antibody affinity against the antigen due to the recognition of multiple epitopes. This ability to detect multiple epitopes also results in more robust detection, and a greater sensitivity for detecting antigens that are present in small quantities in the sample. Polyclonal antibodies are also less sensitive to antigen changes such as slight denaturation, polymorphism, or in the case of NT-proBNP, heterogeneity of glycosylation, than monoclonal antibodies. Polyclonal antibodies also offer advantages in terms of short production time and lower cost.

According to an embodiment of the above aspect and embodiments thereof, the polyclonal antibody and/or the mixture of monoclonal antibodies binds with substantially same affinity to both glycosylated and non-glycosylated forms of NT-proBNP or fragments thereof.

Currently the glycosylation sites of NT-proBNP are held to be amino acids 36, 37, 44, 48, 53 and 58 of SEQ ID NO. 1. Also T71 can be glycosylated, but this is located close to the cleavage site and the convertase-dependent cleavage of proBNP into NT-proBNP and BNP can only occur if T71 is not glycosylated. Consequently, the majority of the unprocessed proBNP found in circulation has an O-glycan on T71 whereas the same amino acid in NT-proBNP is not glycosylated (Semenov et al., Processing of proBNP is suppressed by 0-glycosylation on the region close to the cleavage site, Clin Chem, 2009, 55(3): 489-498).

Preferably the polyclonal antibody and/or the mixture of monoclonal antibodies specifically recognizes more than one epitope of NT-proBNP. The expression "more than one epitope" includes that different (glycosylated or non-glycosylated) epitopes are recognized, and that a plurality of linear or structural epitopes within NT-proBNP are recognized.

The inventors postulate that an assay which is less sensitive to glycosylation of the antigen, or even independent thereof, will result in a more accurate quantification result. In other words, the herein disclosed assay reflects the true concentration of native NT-proBNP in a sample. There are indications that inter-individual variations exist in the glycosylation patterns (Saenger, A. K. et al., Specificity of B-Type Natriuretic Peptide Assays: Cross-Reactivity with Different BNP, NT-proBNP, and proBNP Peptides, Clinical Chemistry, 63:1 (2017) 351-358), and the inventors postulate that the herein described assay and its components will become the basis for a new standard for NT-proBNP assays. An important advantage of the herein described assay is that it doesn't require a pre-treatment such as de-glycosylation of the sample, and thus simplifies handling, increases throughput and removes a possible source of error, otherwise present when additional sample handling steps are involved.

It presents an additional challenge to measure antigen molecules in patient samples when the antigen molecules are present in very low concentrations.

Antigen NT-proBNP concentrations in patient plasma samples at low concentrations, below 200 ng/l and even below 100 ng/l, have previously not been possible to quantify by turbidimetric measurements, partly because of low turbidimetric signal strengths related to the low peptide concentrations, and partly because the glycosylation blockage of detecting antibodies in large parts of the NT-proBNP molecules.

According to an embodiment, the kit includes a mixture of immunoparticles wherein said mixture comprises both immunoparticles coated with polyclonal antibodies or a mixture of monoclonal antibodies which binds to NT-proBNP within the amino acid sequence of SEQ ID NO. 2, and immunoparticles coated with polyclonal antibodies or a mixture of monoclonal antibodies which binds to NT-proBNP within the amino acid sequence of SEQ ID NO. 3.

In an especially advantageous embodiment of the method disclosed herein, immunoparticles coated with antibodies having a high affinity for the peptide of SEQ ID NO. 2 or a fragment thereof are combined with immunoparticles coated with antibodies having a high affinity for the peptide of SEQ ID NO. 3 or a fragment thereof. As a result, a large part of the non-glycosylated sequences of NT-proBNP molecules could be utilized for generating the turbidimetric signal by binding immunoparticles with the antibodies against both peptides of SEQ ID NOs 2 and 3 or fragments thereof, using either polyclonal antibodies or a mixture of monoclonal antibodies, having specific affinity to the peptides of SEQ ID NOs 2 and 3, and/or fragments thereof.

The two peptides identified and chosen by the inventors, i.e the regions represented by SEQ ID NO:s 2 and 3 are both outside the glycosylated region of native NT-proBNP. Several other regions and putative epitopes, partially overlapping or falling within these sequences have been disclosed and used for raising monoclonal antibodies. It is presently held by the inventors that the specific peptides, represented by SEQ ID NOs 2 and 3 or parts thereof, can be used for raising polyclonal antibodies, and optionally also for purifying the antibodies. As disclosed in the context of Example 1, the peptides can be used for raising antibodies, in lieu of the native or recombinant full-length NT-proBNP, and/or for purifying the resulting mixture of antibodies.

Preferably the immunization is performed with a non-glycosylated recombinant antigen, such as one or both the peptides represented by SEQ ID NO. 2 and SEQ ID NO 3, as well as fragments thereof, followed by purification using peptides representing epitopes similar or identical on both glycosylated and non-glycosylated antigens. Using these peptides or peptide fragments as immunogens has an advantage in that the synthesis of a shorter peptide is less costly than the synthesis of the full-length molecule. Different approaches to raising antibodies and purifying the same are shown in Table 2.

According to an embodiment of the above aspect and embodiments thereof, the polyclonal antibody and/or the mixture of monoclonal antibodies binds/bind specifically to NT-proBNP with a $K_D$ to recombinant NT-proBNP of less than 10.0E-09 M, such as less than 5.0E-09 M, preferably less than 2.0E-09 M.

According to another embodiment, the polyclonal antibody and/or the mixture of monoclonal antibodies binds/bind specifically to the peptide of SEQ ID NO. 2 or a fragment thereof with a $K_D$ of less than 5.0E-09 M, preferably less than 2.0E-09 M.

According to yet another embodiment, the polyclonal antibody and/or the mixture of monoclonal antibodies binds/bind specifically to the peptide of SEQ ID NO. 3 or a fragment thereof with a $K_D$ of less than 10.0E-09 M, preferably less than 5.0E-09 M, more preferably less than 2.0E-09 M.

According to another embodiment of the first aspect, freely combinable with the above embodiments, said at least one antibody is a polyclonal antibody or a mixture of monoclonal antibodies, preferably a polyclonal antibody, binding to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9 and/or SEQ. ID. NO. 10.

The method according to claim 1, wherein the particle has an average (mean) size in the range of 150-300 nm, preferably about 150-240, more preferably 180-220 nm in uncoated form. Particle size can be determined using a NanoSight® NS300 instrument (Malvern Panalytical Ltd., Malvern, United Kingdom) according to the manufacturer's instructions.

When a concentration of NT-proBNP is measured nephelometrically, particles with a size in the upper end of the interval are used, and when the concentration of NT-proBNP is measured turbidimetrically, smaller particles can be used. The inventors have tested particles with an average size of 50 nm, 100 nm, 140 nm, 150 nm, 200 nm, 240 nm, and 290 nm and shown that the method works well with particles starting from an average size of 150 nm. A preferred size interval is 160 nm-240 nm, and in particular 180 nm-220 nm. When the particle size exceeds 200 nm, the spontaneous sedimentation of the particles however has to be addressed, for example by adjusting the density of the storage buffer for the immunoparticles. The present inventors have found that the stability can be improved, and the sedimentation of particles can be prevented or at least significantly reduced by consciously adjusting the density of the buffer in which the particles are suspended, and that this can be done without compromising the activity of the immunoreagents, the optical properties of the resulting solution, or the performance of the assay.

A suitable density adjusting agent can be chosen from heavy water (deuterium oxide) and non-ionic water-soluble natural and/or synthetic polymers. The density adjusting agent is preferably chosen from 5-[acetyl-[3-[~{N}-acetyl-3,5-bis(2,3-dihydroxypropylcarbamoyl)-2,4,6-triiodoanilino]-2-hydroxypropyl]amino]-1-~{N},3-~{N}-bis(2,3-dihydroxypropyl)-2,4,6-triiodobenzene-1,3-dicarboxamide (iodixanol, available e.g. as OptiPrep™) and polysucrose (e.g. Ficoll®) and most preferably iodixanol.

Based on their experiments, the inventors concluded that particles in the range of about 180-220 nm in uncoated form are most suitable when the method is performed as a turbidimetric method.

The inventors have surprisingly shown that the coating ratio has relevance for the sensitivity of the method, and thus according to an embodiment of said first aspect, said at least one antibody is coated onto the particle at a coating ratio of 6%, (0.6:10)—60% (6:10), preferably 6% (0.6:10)—30% (3:10), most preferably 10% (1:10)—20% (2:10).

According to an embodiment of the above, the coating ratio is chosen thus, that said at least one antibody is coated onto the particles forming at least one layer, or layers, having a thickness of at least about 10 nm, preferably about 20 nm, and most preferably about 30 nm or more.

Higher coating ratios have also been tested, in particular coating ratios >100%, i.e. where the amount of antibodies exceed the amount of latex particles at the onset of the coating reaction. Without wishing to be bound by theory, the present inventors believe that a high coating ratio may result in "over-loaded" or "super-loaded" particles, which may increase the binding speed of antigens to the particles. The results of the particle size measurements described in Example 4 indicate that a thick layer or multiple layers of antibodies can indeed be coated onto the particles.

According to an embodiment of the first aspect, and any embodiments thereof, a change in reflectance, scattering or transmittance, is determined at a wavelength in the range from 350 to 700 nm, preferably at about 450-550 nm, for example at a wavelength of 546 or 548 nm. A person skilled in the art will realize that the wavelength may be adjusted depending on other parameters of the assay, mainly particle size.

According to another embodiment of the first aspect, freely combinable with any of the other embodiments, the method includes a step of calibration using a calibrator comprising a known concentration of a substance chosen from the peptide of SEQ ID NO. 2, a fragment thereof, the peptide of SEQ ID NO. 3, or a fragment thereof, for example a known concentration of a substance chosen from the peptide of SEQ. ID. NO. 4, SEQ. ID. NO 5, SEQ. ID. NO. 6, SEQ. ID. NO. 7, SEQ. ID. NO. 8, SEQ. ID. NO. 9 and SEQ. ID. NO. 10, or combinations thereof. In the alternative, the calibrator is chosen from native or recombinant full-length NT-proBNP of SEQ ID NO. 1.

It is advantageous to use a short peptide in the calibrator, as it will be faster and cheaper to synthesize a shorter recombinant peptide than to isolate the antigen from natural samples, for example patient samples.

According to another embodiment, the change in reflectance, scattering or transmittance of the sample is a change in transmittance, and the method is performed as a turbidimetric measurement of the concentration of NT-proBNP.

According to another embodiment, the change in reflectance, scattering or transmittance of the sample is a change in reflectance or scattering, and the method is performed as a nephelometric measurement of the concentration of NT-proBNP.

A second aspect of the present disclosure relates to an immunoparticle coated with at least one antibody chosen from a polyclonal antibody or mixture of monoclonal antibodies which specifically binds to NT-proBNP within the amino acid sequence of SEQ ID NO. 2; or which specifically binds NT-proBNP within the amino acid sequence of SEQ ID NO. 3.

According to a preferred embodiment of said second aspect, said at least one antibody specifically binds to NT-proBNP within the amino acid sequence of SEQ ID NO. 2.

According to an embodiment of said second aspect, the polyclonal antibody and/or the mixture of monoclonal antibodies binds with substantially same affinity to both glycosylated and non-glycosylated forms of NT-proBNP.

According to a further embodiment, the polyclonal antibody and/or the mixture of monoclonal antibodies binds specifically to NT-proBNP within the amino acid sequence of SEQ ID NO. 2 or the amino acid sequence of SEQ ID NO. 3 and exhibits a $K_D$ to NT-proBNP of less than 5.0E-09, preferably less than 2.0E-09 M. In a preferred embodiment, the affinity to NT-proBNP is determined by measuring the $K_D$ to recombinant NT-proBNP.

According to a further embodiment, the at least one antibody is a polyclonal antibody or a mixture of monoclonal antibodies, preferably a polyclonal antibody, binding to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9, and/or SEQ. ID. NO. 10.

According to an embodiment of said second aspect, freely combinable with all other embodiments, said immunoparticle has a core consisting of a particle having an average size in the range of 150-300 nm, preferably about 150-240 nm, more preferably 160-240 nm, most preferably 180-220 nm in uncoated form. In one embodiment, the particle is a latex particle.

A third aspect relates to a kit for particle enhanced optical determination of a concentration of NT-proBNP in a sample, said kit comprising:

at least one antibody which specifically recognizes and binds to NT-proBNP within the amino acid sequence of SEQ ID NO. 2 or SEQ ID NO. 3, wherein said at least one antibody is immobilized to a particle;

a calibrator, and optionally, instructions for using the kit to determine the concentration of NT-proBNP in the sample.

Preferably the particle is an immunoparticle according to the second aspect or any embodiment thereof.

According to an embodiment of said third aspect freely combinable with the above, the calibrator comprises a known amount of the peptide of SEQ ID NO.

2, a fragment thereof, the peptide of SEQ ID NO. 3, or a fragment thereof, or a combination thereof. In the alternative, the calibrator is chosen from native or recombinant full-length NT-proBNP of SEQ ID NO. 1.

The kit according to the above, further comprising a storage buffer in which the immunoparticles are suspended, wherein the storage buffer comprises a density gradient medium and the density of said storage buffer is adjusted to substantially the same specific weight as the specific weight of the immunoparticles. A suitable density adjusting agent can be chosen from heavy water (deuterium oxide) and non-ionic water-soluble natural and/or synthetic polymers. The density adjusting agent is preferably chosen from 5-[acetyl-[3-[~{N}-acetyl-3,5-bis(2,3-dihydroxypropylcarbamoyl)-2,4,6-triiodoanilino]-2-hydroxypropyl]amino]-1-~{N},3-~{N}-bis(2,3-dihydroxypropyl)-2,4,6-triiodobenzene-1,3-dicarboxamide (iodixanol, available e.g. as OptiPrep™) and polysucrose (e.g. Ficoll®) and most preferably iodixanol.

According to an embodiment, the kit further comprises an assay buffer, said assay buffer comprising PEG in a concentration of 0.05-0.5, preferably 0.05-0.4% weight/volume.

According to another embodiment, freely combinable with other embodiments of this third aspect, the assay buffer comprises a blocking agent, for example 0.001-2% of a suitable protein such as albumin of different species (bovine, rabbit, chicken). According to one embodiment the blocking agent is IgG in a concentration of about 0.1%.

According to yet another embodiment, freely combinable with other embodiments of this third aspect, said particle enhanced optical method is chosen from nephelometry and turbidimetry.

A fourth aspect of the present disclosure relates to a method for identifying a subject with heart failure or having an elevated risk for heart failure by determining the concentration of NT-proBNP in a bodily fluid sample of said subject, said method comprising:
providing an immunoparticle according to the second aspect or any embodiments thereof;
reacting the sample with said immunoparticle;
detecting a change in reflectance or transmittance of the sample, wherein the change in reflectance, scattering or transmittance of the sample is indicative for the amount of NT-proBNP; and
determining if said concentration of NT-proBNP in said sample is elevated above a selected control cut-off concentration;
wherein said elevated concentration of NT-proBNP is an indication that the subject has heart failure or an elevated risk for heart failure.

According to an embodiment of said fourth aspect, the sample is a sample chosen from blood plasma and blood serum and the change in reflectance, scattering or transmittance is a change in transmittance and the method is a turbidimetric method.

According to an embodiment of the above, the sample is a sample chosen from blood plasma and blood serum and the change in reflectance, scattering or transmittance is a change in reflectance or scattering and the method is a nephelometric method.

It is a significant advantage that the method can be performed as turbidimetric or nephelometric method, as such methods can be automated, and performed on existing clinical analysers, available in practically all clinical chemistry laboratory globally.

A fifth aspect relates to a polyclonal antibody or a mixture of monoclonal antibodies, binding specifically to NT-proBNP and which exhibits a $K_D$ to recombinant NT-proBNP of less than 5.0E-09, preferably less than 2.0E-09 M.

According to an embodiment of the fifth aspect, said polyclonal antibody or mixture of monoclonal antibodies is capable of specifically recognizing and binding to both glycosylated and non-glycosylated forms of recombinant NT-proBNP with substantially same affinity.

Preferably said polyclonal antibody or mixture of monoclonal antibodies is further capable of specifically recognizing and binding to NT-proBNP within the amino acid sequence of SEQ ID NO. 2 and/or the amino acid sequence of SEQ ID NO. 3.

According to an embodiment of the fifth aspect, the polyclonal antibody or mixture of monoclonal antibodies are capable of binding to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9 and/or SEQ. ID. NO. 10.

A sixth aspect relates to the use in vitro of a polyclonal antibody which specifically binds to NT-proBNP and which exhibits a $K_D$ to recombinant NT-proBNP of less than 5.0E-09 M in diagnosis, monitoring, stratifying or predicting mortality rate in patients with heart failure or identifying subjects at risk of developing heart failure.

According to an embodiment thereof, said polyclonal antibody binds to a synthetic peptide chosen from the peptide comprising or consisting of the amino acids of SEQ ID NO. 2, and the peptide comprising or consisting of the amino acid residues of SEQ ID NO. 3.

According to an embodiment of the sixth aspect, said polyclonal antibody or mixture of monoclonal antibodies, preferably a polyclonal antibody, binds to at least one epitope chosen from the epitopes consisting of the amino acids of SEQ. ID. NO. 4, SEQ. ID. NO 5, SEQ. ID. NO. 6, SEQ. ID. NO. 7, SEQ. ID. NO. 8, SEQ. ID. NO. 9 and/or SEQ. ID. NO. 10.

The results achieved by the inventors indicate that NT-proBNP can be measured quantitatively using turbidimetric methods. In addition, or alternatively, the choice of antibodies, the excess loading of antibodies to the particles, and/or the choice of epitopes, can make it possible to measure a higher proportion of the total NT-proBNP in the sample, e.g. even 5 times higher concentrations compared to current commercial assays which may only measure non-glycosylated NT-proBNP.

Specific advantages have been presented in association with selected features and other advantages will be apparent to a person skilled in the art upon study of the following examples which illustrate the inventions.

EXAMPLES

Example 1. Production of Antibodies

Antibodies were produced in either a mammalian host (rabbit or goat), or in an avian host (hens) against different immunogens and purified as shown in Table 2 below.

TABLE 2

Overview of antibody production

| Host | Immunogen | Purified against |
|---|---|---|
| Mammalian (Rabbit or | NT-proBNP (recombinant, | NT-proBNP (recombinant, entire molecule, non-glycosylated, HyTest) |

TABLE 2-continued

Overview of antibody production

| Host | Immunogen | Purified against |
|---|---|---|
| goat) | entire molecule) | Peptide 1 (SEQ. ID. NO. 2) |
|  |  | Peptide 2 (SEQ. ID. NO. 3) |
|  |  | proBNP (recombinant, glycosylated, HyTest) |
|  | Peptide 1 + KLH | NT-proBNP (recombinant, entire molecule, non-glycosylated, HyTest) |
|  |  | Peptide 1 (SEQ. ID. NO. 2) |
|  |  | proBNP (recombinant, glycosylated, HyTest) |
|  | Peptide 2+ KLH | NT-proBNP (recombinant, entire molecule, non-glycosylated, HyTest) |
|  |  | Peptide 2 (SEQ. ID. NO. 3) |
|  |  | proBNP (recombinant, glycosylated, HyTest) |
| Avian (hen) | NT-proBNP (recombinant, entire molecule) | NT-proBNP (recombinant, entire molecule, non-glycosylated, HyTest) |
|  |  | Peptide 1 (SEQ. ID. NO. 2) |
|  |  | Peptide 2 (SEQ. ID. NO. 3) |
|  |  | proBNP (recombinant, glycosylated, HyTest) |
|  | Peptide 1 | NT-proBNP (recombinant, entire molecule, non-glycosylated, HyTest) |
|  |  | Peptide 1 (SEQ. ID. NO. 2) |
|  |  | proBNP (recombinant, glycosylated, HyTest) |
|  | Peptide 2 | NT-proBNP (recombinant, entire molecule, non-glycosylated, HyTest) |
|  |  | Peptide 2 (SEQ. ID. NO. 3) |
|  |  | proBNP (recombinant, glycosylated, HyTest) |

Antibodies against NT-proBNP and variants thereof (for example recombinant or native, truncated or non-truncated forms, glycosylated and non-glycosylated forms, and combinations thereof) can be produced according to methods known to a person skilled in the art, either in mammal hosts, e.g. goats or rabbits, or preferably in hens, in which case the antibodies can be isolated from the egg yolk. Two peptides designated "Peptide 1" and "Peptide 2" were synthetized (Genscript Biotech (Netherlands) B. V., Leiden, The Netherlands), delivered as a white lyophilized powder with >90% HPLC purity, and used as immunogens, in addition to the recombinant, full-length NT-proBNP in glycosylated and non-glycosylated form:
HPLGSPGSAS DLETSGLQEQ RNHLQGKLSE LQVEQTSLEP LQESPRPTGV WKSREVATEG IRGHRKMVLY TLRAPR (Full-length NT-proBNP, SEQ ID NO. 1)
SAS DLETSGLQEQ RNHLQGKLSE LQV (SEQ ID NO. 2, Peptide 1, amino acid residues 8-33 of SEQ ID NO. 1)
IRGHRKMVLY TLRA (SEQ ID NO. 3, Peptide 2, amino acid residues 61-74 of SEQ ID NO. 1)

When raising antibodies against a shorter peptide, such as Peptide 1 or Peptide 2, these are preferably conjugated to a suitable carrier to increase immunogenicity. One example is keyhole limpet hemocyanin (KLH) used in the immunization of the mammalian hosts (rabbits). Immunization and antibody purification protocols for raising polyclonal rabbit antibodies are well-known to a person skilled in the art, and available for example from CBG, Max Planck Institute of Molecular Cell Biology and Genetics. General procedures are also disclosed in Antibodies: A Laboratory Manual, Edward A. Greenfield (Ed.), Cold Spring Harbor Laboratory, Cold Spring Harbor, N.Y., 2012.

Avian immunoglobulin fractions such as those used in this assay can be purified from eggs from immunized hens, immunized with native or recombinant NT-proBNP or variants thereof, as indicated in Table 2. The antigen and suitable adjuvant, e.g. complete Freund's adjuvant, is injected subcutaneously and/or intramuscularly into breast tissue of the hen. Immunizations are repeated at regular intervals, for example on day 10, 20 and 30. Antibodies are usually detected in the eggs by day 30.

Eggs are collected, the yolk separated from the white, and the immunoglobulin fraction is isolated from the egg yolk. As a first step, the lipids and lipoproteins are removed, using a suitable method known to persons skilled in the art, for example precipitation using PEG or dextran sulphate, solubilisation using organic solvents, or ultrafiltration. The resulting substantially lipid-free solution can then be concentrated and purified to obtain the desired immunoglobulin fraction containing polyclonal antibodies against the antigen.

The immunisation of rabbits was performed by GenScript Biotech Corp., Piscataway, N.J., USA, and the immunization of hens by Norwegian Antibodies AS, NABAS, As, Norway. All antibodies were purified by Getica A B, Gothenburg, Sweden.

Goat IgG was produced by InnovaGen AB, Lund, Sweden, immunizing goats with a peptide according to SEQ ID NO. 2 and SEQ ID NO. 3, following the same methods, mutatis mutandis. Methods for the concentration and/or purification of immunoglobulins are also well known to a person skilled in the art and include precipitation steps using for example PEG or sodium sulphate, or other well-known methods such as ultrafiltration or liquid chromatography. For more guidance, see e.g. Antibodies: A Laboratory Manual, Edward A. Greenfield (Ed.), Cold Spring Harbor Laboratory, Cold Spring Harbor, N.Y., 2012.

Polyclonal antibodies against the peptides of SEQ ID NO 2 and SEQ ID NO. 3 also achieved high affinity (See Example 2 below) and high specificity, avoiding binding to glycosylated regions, which allows the measurement of the true NT-proBNP concentration with high sensitivity also in a turbidimetric or nephelometric setting.

Example 2. Biacore™ Affinity Analysis

As part of the quality assurance in the production of antibodies for the experiments disclosed herein, affinity analysis was routinely performed for each batch. The affinity of an antibody for its antigen is determined by surface plasmon resonance (SPR) in a method often referred to as the Biacore™ method. SPR occurs under conditions of total internal reflection of plane-polarized light at an interface between two media of different refractive index, coated with an electrically conducting film. When a sample binds to the surface, the refractive index increases, and the resonance angle changes. The angle is monitored continuously as the SPR signal, and a plot of the signal against time, called a sensorgram, shows the changes in refractive index as a sample binds to and dissociates from the surface.

The analysis was performed using a Biacore™ X100 system, using the GE Sensor Chip CM5 (all from GE Healthcare). The chip has a gold surface with a dextran matrix having carboxyl groups on it. For determining the affinity of an antibody to an antigen, the surface of a chip is activated, and an antigen is covalently attached to the surface. This process is irreversible, so the chip can be re-used several times without the need for extra antigen.

For determining the kinetic constants, the target antibodies were first dialysed against PBS and then diluted in HBS to 30 nanomolar (nM). A dilution series was prepared (30 nM-10 nM-3.3 nM-1.1 nM and 0.37 nM) for each target antibody. The concentration was confirmed by spectrophotometric analysis at 280 nm.

The antibodies were analysed on the Biacore™ X100 system, using the Biacore™ X100 Control Software, which when executed on the system injects the antibody dilution series in reverse (starting with the most diluted) sequentially and as a final step the surface is re-generated with glycine (pH 1.5). The kinetic constants are extracted from the sensorgram using the Biacore™ X100 Evaluation Software based on a 1:1 kinetic model. FIG. 3 show the sensorgram from a Biacore™ affinity analysis for IgG antibody from rabbit antiserum, purified against non-glycosylated recombinant NT-proBNP, and tested against a Biacore™ chip with the full-length antigen. The equilibrium dissociation constant was determined to $K_D$=1.35E-09 M.

Similarly, FIG. 4 shows the Biacore™ affinity results for IgY antibody purified against Peptide 1 (SEQ ID NO. 2) and tested against a Biacore™ chip with the full-length antigen. The equilibrium dissociation constant was determined to KD=2.11E-09 M. Typical results of the Biacore™ analysis are summarized in Table 3 below:

TABLE 3

Dissociation constants

| Host | Immunogen | Purified against | Biacore™ data (dissociation constant, $K_D$, molar (M)) |
|---|---|---|---|
| Mammalian (rabbit) | Recombinant NT-proBNP, entire molecule | Recombinant NT-proBNP, entire molecule, non-glycosylated | 1.35E−09 |
|  |  | Peptide 1 | 8.67E−10 |
|  |  | Peptide 2 | 1.26E−09 |
| Avian (hen) | Recombinant NT-proBNP, entire molecule | Recombinant NT-proBNP, entire molecule, non-glycosylated | Average 5E−09 (several different lots tested) |
|  |  | Peptide 1 | 1.98E−09 |
|  |  | Peptide 2 | 1.72E−07 |
|  |  | proBNP (recombinant, glycosylated) | 5.24E−09 |

The results showed that the immunisation protocol and purification consistently produced antibodies binding specifically to NT-proBNP and exhibiting a $K_D$ to recombinant NT-proBNP of less than 2.0E-09 M.

The affinity constants were plotted against the span response and the sensitivity of the assay when run on a clinical chemistry analyser (Mindray® BS-400). As seen in FIGS. 5 and 6, there is a clear correlation between span, sensitivity and the dissociation constants.

IgG antibody against the peptide of SEQ ID NO 2 from goat antiserum, purified against the same peptide, was tested against a Biacore™ chip with the peptide of of SEQ ID NO 2. The equilibrium dissociation constant was determined to $K_D$=2.64E-09 M.

IgG antibody against the peptide of SEQ ID NO 3 from goat antiserum, purified against the same peptide, was tested against a Biacore™ chip with the peptide of of SEQ ID NO 3. The equilibrium dissociation constant was determined to $K_D$=9.72E-09 M.

Similarly, IgG antibody against the peptide of SEQ ID NO 3 from rabbit antiserum was tested against a Biacore™ chip with the peptide of of SEQ ID NO 3. The equilibrium dissociation constant was determined to $K_D$=6.54E-09 and 5.23E-09 M.

Example 3. Epitope Mapping

Epitope mapping was performed by Pepscan Presto BV, Lelystad, The Netherlands, using libraries of linear and looped peptide arrays synthesised onto a solid support covered with a hydrogel. The mapping technique was first published in 1984 (Geysen et al., Use of peptide synthesis to probe viral antigens for epitopes to a resolution of a single amino acid, PNAS, Jul. 1, 1984 81 (13) 3998-4002, incorporated by reference). Chicken and rabbit antibodies were provided by Gentian A S, and the mapping focused on a 26 residues long segment of the NT-proBNP sequence, positions 8-33, sequence SASDLETSGLQEQRNHLQGKLSELQV (identical to SEQ ID NO. 2).

Synthesis of peptides: To reconstruct epitopes of the target molecule a library of peptide-based peptide mimics was synthesized using Fmoc-based solid-phase peptide synthesis. An amino functionalized polypropylene support was obtained by grafting with a proprietary hydrophilic polymer formulation, followed by reaction with t-butyloxycarbonyl-hexamethylenediamine (BocHMDA) using dicyclohexyl-carbodiimide (DCC) with N-hydroxy-benzotriazole (HOBt) and subsequent cleavage of the Boc-groups using trifluoro-acetic acid (TFA). Standard Fmoc-peptide synthesis was used to synthesize peptides on the amino-functionalized solid support by custom modified JANUS liquid handling stations (Timmerman et al., (2007) Functional reconstruction and synthetic mimicry of a conformational epitope using CLIPS™ technology, J. Mol. Recognit. 20:283-299; and Langedijk et al. (2011) Helical peptide arrays for lead identification and interaction site mapping, Analytical Biochemistry 417:149-155, incorporated by reference).

In a first set, linear peptides of a length ranging from 5-24 derived from the target sequence/SEQ ID NO. 2) were synthetized with an offset of one residue. In a second set, constrained peptides of length 7-27 were synthesized starting from Linear peptides of length 5-25 residues derived from the target sequence of NT Pro BNP with an offset of one residue were placed between two Cys residues. Cys residues were joined by mP2 CLIPS in order to create a loop mimic.

The binding of antibody to each of the synthesized peptides was tested in an

ELISA. The peptide arrays were incubated with primary antibody solution overnight at 4° C. After washing, the peptide arrays were incubated with a 1/1000 dilution of an appropriate antibody peroxidase conjugate for one hour at 25° C. After washing, the peroxidase substrate 2,2"-azino-di-3-ethylbenzthiazoline sulfonate (ABTS) and 20 µl/ml 3% $H_2O_2$ were added. After one hour, the color development was measured. The color development was quantified with a charged coupled device (CCD)-camera and an image processing system.

The main epitope candidates identified in this study are presented in the table below:

TABLE 4

| Epitope candidates based on epitope mapping | |
|---|---|
| Amino acid sequence | SEQUENCE ID. NO. |
| SASDL | SEQ. ID. NO. 4 |
| DLETSGLQEQRNHL | SEQ. ID. NO. 5 |
| NHLQGKL | SEQ. ID. NO. 6 |
| SASDLETS | SEQ. ID. NO. 7 |

TABLE 4-continued

Epitope candidates based on epitope mapping

| Amino acid sequence | SEQUENCE ID. NO. |
|---|---|
| ETSGLQ | SEQ. ID. NO. 8 |
| GKLSELQ | SEQ. ID. NO. 9 |
| GLQEQR | SEQ. ID. NO. 10 |

Example 4. Coating of Latex Particles

Latex particles (Ikerlat Polymers S.L., Spain) of different sizes were coated with antibodies produced as in Example 1. Particles of different sizes were investigated. The following particle sizes (reported by the supplier) were investigated: 50, 100, 140, 150, 200 and 290 nm. Based on their experiments, the inventors concluded that particles in the range of about 180-220 nm in uncoated form are most suitable when the method is performed as a turbidimetric method. But also particles in the range of 150 nm-180 nm perform well in the method. For nephelometric methods, also encompassed by the present description and claims, immunoparticles up to a size of 320 nm were found to be very usable, while the best results were obtained using particles having a size of 270-300 nm.

The following general coating procedure was followed: An aliquot of antibodies (e.g. 10 mg IgG) was dialysed into a boric acid and NaCl buffer, pH 9.5. When the particles were not already chloromethylated, an activating step was included before the particles were mixed with IgG at various coating ratios. The mixtures where then incubated, for example at 37° C. for 3 days. A blocking buffer comprising 1 mg/ml rabbit serum albumin in boric buffer was added, and the mixture incubated overnight. A first dilution buffer comprising 10 mM boric acid, 15 mM NaCl, glycine, Tween®, ProClin™, and rabbit serum albumin, pH 9.5 was added, and the mixture incubated overnight at 37° C.

The particles with conjugated antibodies were then washed twice with a dialysis buffer comprising 5 mM boric acid, 7.5 mM NaCl, Tween®, ProClin™, and rabbit serum albumin, pH 8.8, and finally washed twice with TRIS buffer, pH 8.8.

In one experiment, 150 nm latex particles were coated with goat IgG antibodies raised against the peptide of SEQ ID NO. 2 as follows:

14 mg goat anti human NT-proBNP (Getica Aft Sweden) antibodies were dialyzed in a Slide-A-Lyzer® 10000 MWCO in 7.5 mM NaCl, 5 mM boric acid, pH. 9.33 resulting in about 14 mg antibodies in 56 ml 7.5 mM NaCl, 5 mM boric acid, pH 9.3 at the end of the dialysis.

A 4% particle suspension (0.625 ml=0.625*40=25 mg) of 150 nm diameter latex particles (Thermo Fisher Scientific, Cat. No. C 29369, packaging lot number 1555355) was washed by dialysis in purified water and mixed with the above 14 mg goat IgG, and reacted under stirring during 24 hours at 44° C. The resulting mixture was centrifugated and the supernatant removed by suction.

To this 10 ml of a solution of 5 mM boric acid, 7.5 mM NaCl, 1.5 mM glycine 0.25 g/l Tween® 20, 0.25 g ProClin™ per l with 1 mg/ml goat albumin was added. The mixture was stirred for 10 hours at 44° C.

The resulting mixture was centrifuged at 8000 rpm for 60 minutes. The supernatant was removed by suction, and the mixture resuspended in 25 ml buffer (7.5 mM NaCl, 5 mM boric acid, 1.5 mM glycine, 0.25 g/l Tween® 20, 0.25 g ProClin™ per with 1 mg/ml goat albumin). This step was repeated 3 times.

The resulting particles were suspended in 10 ml storage buffer comprising 7 mM boric acid, 7.5 mM NaCl, 1.5 mM glycine, 0.25 g/l Tween® 20, 0.25 g ProClin™ per l, and 1 mg/ml goat albumin.

Different amounts of IgG were loaded onto latex particles, investigating the effects of different coating ratios, e.g. 6%, 15%, 60%, 90%, 120% and 150%. The term "coating ratio" here refers to the amount of antibody in relation to the amount of latex particles at the start of the coating reaction. For example, 0.5 mg IgG to 1 mg latex particles represents a coating ratio of 50%, 1 mg IgG to 1 mg particles represents a ratio of 100% and so on.

Example 5. Particle Size Analysis

An immunoparticle lot was made with 200 nm latex particles and a 10% coating ratio following the general procedure disclosed in Example 4 and subjected to particle size measurement. FIG. 7 shows the size distribution of immunoparticles determined using a NanoSight® NS300 instrument (Malvern Panalytical Ltd., Malvern, UK). The results confirm that a substantially homogenous lot was achieved.

The size of uncoated and coated particles (latex particles, Ikerlat AJ20CH2C1-L3, 199±2 nm, Ikerlat Polymers S.L., Spain) was analysed using a NanoSight® NS300 instrument (Malvern Panalytical Ltd., Malvern, United Kingdom) according to the manufacturer's instructions.

The results are summarized in Table 5 below and illustrated in FIG. 8.

TABLE 5

Particle size measurements

| Particle Lot | Plain latex, Mean | Plain latex, mode | Coated mean | Coated, Mode | Difference mean | Difference mode | Ratio IgG/Latex |
|---|---|---|---|---|---|---|---|
| L18a | 187 | 183 | 193 | 195 | 6 | 12 | 6% |
| L18b | 187 | 183 | 232 | 198 | 44 | 10 | 15% |
| L18c | 187 | 183 | 264 | 216 | 77 | 32 | 60% |
| L18d | 187 | 183 | 228 | 210 | 41 | 27 | 90% |
| L18e | 187 | 183 | 216 | 207 | 29 | 24 | 120% |
| L18f | 187 | 183 | 226 | 205 | 38 | 22 | 150% |

The size of an antibody can be estimated to about 10 nm in length. Thus, the results of the measurements done on the particles L18a-f, indicate that overloading the particles with antibodies results in more than one layer of antibodies on the particles. An even monolayer would theoretically increase the particle diameter by about 20 nm, and a double layer by about 40 nm. The diameter increase of 77 nm which was achieved at the 60% ratio (IgG/latex) indicates that up to four layers of antibodies are present on the particle. There however appears to be a drop-off in coating efficiency at about 50-60% ratio of antibodies to latex. Without wishing to be bound by theory, the inventors believe that the antibodies do not form even layers, but instead accumulate on the particle, forming a porous network of antibodies.

Again, without wishing to be bound by theory, the inventors believe that for small analytes, the analyte can penetrate into this network of antibodies. Thus, a particle overloaded with antibodies as disclosed in the present description and examples, is likely to have a significantly larger effective surface than a conventionally produced particle.

Preliminary experiments indicated that the sensitivity and response increase with increasing antibody loading. Based on the results of the measurements done on lots L18a through L18f, it is concluded that overloading the particles with antibodies resulted in the creation of more than one layer of antibodies on the particles. Based on the diameter increase, it is contemplated that overloading the particles results in structures as illustrated in FIG. 9.

Example 6. Development and Validation of Assay Components

Immunoassay systems require calibration protocols that are normally more sophisticated than many analytical techniques in routine clinical use. Calibrators used in such assays may differ significantly from the analyte in clinical specimens. Differences in the properties of calibrators, or reference materials, from those of clinical specimens may include the species origin of the calibrator for an analyte; integrity of the molecular species; matrix of the calibration solution, and addition of preservative agents.

Brain natriuretic peptide (BNP) and the N-terminal fragment of the BNP precursor (NT-proBNP) are widely used biomarkers for heart failure (HF). Since the discovery of BNP in 1988, much effort has been allocated to the precise detection of BNP and NT-proBNP levels for reliable HF diagnostics. As a result, measurements of these biomarkers are globally accepted and used in clinical practice for the diagnosis of acute and chronic HF, risk stratification, and monitoring response to therapy. Several immunoassays specific for BNP and NT-proBNP are currently commercially available. Recent comparative studies however indicate that there are marked differences between different BNP and NT-proBNP assays and platforms, and the results of measurements are not sufficiently comparable.

This lack of equivalence between the assays complicates the interpretation of the results and as a result, the cut-off points used for diagnostic decisions are method dependent. Presently, there is no agreement on what kind of BNP or NT-proBNP standard should be used for calibration, and certified reference material as well as reference measurement procedures are lacking.

The multiple circulating BNP fragments, along with proBNP and NT-proBNP, collectively form the B-type natriuretic peptide family. Immunoassays for BNP utilize a variety of antibodies, both monoclonal and polyclonal, and diverse calibrator materials. Therefore, there are substantial differences in patient specimens between BNP methods, even for assays that use identical antibody configurations on different analytical platforms.

NT-proBNP assays are generally considered harmonized because all utilize calibrators from the same manufacturer (Roche Diagnostics) which are then configured to other manufacturers' immunoassay platforms. However, there are still analytical differences between NT-proBNP assays from different manufacturers that can be attributed partially to different specimen types and platforms, indicative of a larger need for global standardization of NP-proBNP assays.

Previous studies have demonstrated that proBNP and NT-proBNP are glycosylated to varying degrees that can interfere with commercial immunoassays used to quantify NPs in clinical practice (e.g. Saenger et al., 2017). The extent to which these immunoassays exhibit cross-reactivity to B-type natriuretic peptides as well as with their glycosylated and non-glycosylated forms is an important question to elucidate, as this may affect the clinical performance of the assays with implications for patient care. Furthermore, there are currently no formal efforts to standardize or maintain harmonization of BNP or NT-proBNP assays, primarily owing to the known differences in antibodies used and lack of a primary reference standard material.

Calibrator

The results generated by the immunoassay method disclosed herein is of course very much influenced by the values assigned to the calibrator material used in the turbidimetric immunoassay. The values assigned to calibrator material is well described in the prior art, a good example being the protocols developed by Dr. Blirup-Jensen (Blirup-Jensen, S. et al., Protein Standardization IV: Value Transfer Procedure for the Assignment of Serum Protein Values from a Reference Preparation to a Target Material, Clin Chem Lab Med 2001; 39(11): 1110-1122).

The values for the calibrator materials used in the turbidimetric immunoassays disclosed herein was regulated to suit the target for the value transfer procedure of the assay according to Blirup-Jensen et al.

The calibrator material can be constituted by serum or plasma materials from human or animal serum or plasma materials. The calibrator material can further comprise a salt solution, like solutions of PEG-6000 (or other PEG materials) and preservative agents. The composition of the calibrator can be adjusted until the assay method generates results corresponding to values obtained for reference samples (e.g. assay results obtained with commercial assay reagents).

In one experiment, plasma samples with concentration of NT-proBNP (determined by the commercial Roche method) of 4040 ng/L and 5480 ng/L were pooled for further dilution with a low plasma sample (65 ng/L—Roche method). The samples 4040 ng/L and 5480 ng/L were analysed turbidimetrically on a Mindray® clinical analyser and returned absorbance values between 2000 and 3000.

The final concentration of the pooled plasma sample was calculated to 4330 ng/L, and from this, 5 calibrators were made by diluting the 4330-sample with the low sample into the following range: 150 ng/L, 300 ng/L, 800 ng/L, 1500 ng/L, 3200 ng/L. The low sample (65 ng/L) was used as the 0 calibrator.

In another experiment, a stock solution of the peptide of SEQ ID NO. 2 was prepared from dry peptide, supplied by Genscript, The Netherlands and dissolved in 50 mM TRIS, 150 mM NaCl, 0.05% BSA, 0.01% Tween® 20, 0.1% ProClin™, pH=7.8, resulting in a stock solution of 900 µg peptide per ml.

A calibrator for calibrating the assay was made by dilution of said stock solution in plasma from a blood donor testing below 20 ng/l obtained from an external blood bank.

Full-length recombinant NT-proBNP can also be used as calibrator. Calibrators were prepared in TRIS-HCl buffer using recombinant NT-proBNP (>95% purity, Catalogue No. 8NT2, HyTest Ltd., Turku, Finland) to estimated concentrations 0, 94, 188, 376, 750 and 1500 ng/L respectively. Calibration curves were recorded using Lot15B, where antibodies were raised as disclosed in Example 1 and coated onto particles as disclosed in Example 3. The following assay buffer and application settings were used. R1: 12.5 mM MOPS, 600 mM NaCl, 0.4% PEG, pH 7.2, and the R1-R2-Sample-Wavelength-Reading cycle was: 150-20-15-380-43/79. The calibrator set was stored at 4° C. for 2 months before another curve was recorded, using the same measuring conditions. FIG. 10 shows the excellent stability of the calibrator.

In industrial assay production it is not practical to use materials totally or even partly based on patient serum and plasma. In the methods disclosed herein, antigenic material such as the synthetic peptides of SEQ ID NO. 2 and SEQ ID NO. 3 or fragments thereof is/are used to generate a turbidimetric or nephelometric signal based on reactions between the antigen and immunoparticles carrying antibodies binding to SEQ ID NO. 2 and SEQ ID NO. 3 or fragments thereof. Also the full-length NT-proBNP molecule can be used as a calibrator.

The composition of the reagents is/are then adjusted, for example as described by Blirup-Jensen et al. so that the NT-proBNP values from the turbidimetric immunoassay is calibrated to the target material, and the assay results in values according to the calibration which is the aim of the assay. The assay buffer can for example be adjusted to give a response corresponding to the response obtained from a reference preparation. The assay buffer can for example be adjusted until corresponding to the response from a Roche reference assay if the Roche calibration is the target calibration.

Assay Buffer

An appropriate assay buffer was prepared by mixing soluble substances like polyethylenglycol and other soluble polymers and salts and pH buffering substances, and the composition adjusted until the turbidimetric signal of the assay results in a calibration of the assay corresponded to the target calibration, such as the Roche NT-proBNP assay calibration. The assay buffer composition can also be adjusted so that the results correspond to a calibration using a reference method measuring the total concentration of NT-proBNP, comprising both glycosylated and non-glycosylated forms of NT-proBNP, or to other target calibrations corresponding to reference and/or standardized calibrations for methods for the determination of NT-proBNP in samples of body liquids.

The salinity of the assay buffer was varied by adding different amounts of NaCl to the buffer, for example 150, 210, 225, 300 and 450 mM NaCl, added to 12.5 mM MOPS, 0.4% PEG, 0.1% IgG, 0.1% ProClin™, and pH 7.2

The immunoparticles (Lot 46) were supplied in the same storage buffer (R2) in both runs: 1 mg/mL immunoparticles suspended in Tris buffer. First, a 2 mg/mL solution of the immunoparticles was sonicated for 30 sec before dilution to 1 mg/mL with Tris buffer. The assay settings were the same in both runs performed on a Mindray® clinical analyser: R1 150 µL|R2 25 µL|sample 5 µL. The calibrator range was 0-150-300-800-1500-3200 ng/L.

The results show that the assay could be fine-tuned by adjusting the ionic strength of the assay buffer, and the response values could be adjusted to correspond with analysis of the corresponding samples using the Roche Assay reagents at the Academic University Hospital in Uppsala, Sweden. The results are shown in FIG. 11.

Example 7. Analysis of Patient Samples 28 frozen plasma samples with NT-proBNP concentrations ranging from 0-4430 ng/L (assigned with Roche Elecsys®) were obtained.

Calibrators were prepared by first dissolving Peptide 1 (Genscript Biotech (Netherlands) B.V., Leiden, The Netherlands) in Tris-HCl buffer. The dissolved Peptide 1 was then added to NT-proBNP free plasma (plasma from a blood donor testing below 20 ng/l obtained from an external blood bank) to estimated concentrations 0, 130, 500, 1000, and 4000 ng/L, respectively, adjusted to the Roche method.

Antibodies were raised as disclosed in Example 1 and coated onto particles as disclosed in Example 3.

A particle-enhanced turbidimetric immunoassay (PETIA) was set up. An assay buffer comprising 12.5 mM MOPS, 210 mM NaCl, 0.4% PEG, 0.1% IgG, 0.1% ProClin™, pH 7.2 was used. The assay can be operated manually but is preferably run on an automated clinical chemistry instrument. A person skilled in the art can optimize the parameter settings for the assay on any suitable automated clinical chemistry instrument.

The assay was run on a clinical chemistry analyser (Mindray® BS-400, Shenzhen Mindray® Bio-Medical Electronics Co., Ltd., China) with the following settings shown in Table 6 where the R1-R2-Sample-Wavelength-Reading cycle was: 150-25-5-546-43/79.

TABLE 6

| PETIA parameters in Mindray BS-400 | |
|---|---|
| Parameter | Setting |
| Sample volume [µL] | 5 |
| R1: Assay buffer volume [µL] | 150 |
| R2: Reagent volume [µL] | 25 |
| Wavelength [nm] | 546 |
| Reading time | cycle 43-79 |

The assays according to the present invention are based on antibodies directed towards the peptides of SEQ ID NO. 2 and SEQ ID NO 3, regions of the NT-proBNP molecules that are not covered by glycosylation. As described in Example 6, the calibration of the turbidimetric NT-proBNP immunoassay of the invention can be adjusted to obtain good correlation.

Calibration curves are shown in FIGS. 12 and 13, for peptide 1 (SEQ ID NO. 2) and peptide 2 (SEQ ID NO. 3) respectively. FIG. 12 shows a calibration curve for lot 46 (200 nm particles coated with antibodies raised against the peptide of SEQ ID NO. 2 (Peptide 1)), using the same peptide (SEQ ID. 2) as calibrator antigen. FIG. 13 shows a calibration curve for lot 49 (200 nm particles coated with antibodies raised towards the peptide of SEQ ID NO 3 (Peptide 2)), using native antigen as calibrator antigen. It is seen that antibodies are capable of reacting with varying concentrations of antigen in a linear fashion.

FIG. 14 is a graph comparing the results (ng/l) of 28 turbidimetric measurements of NT-proBNP using immunoparticles coated with antibodies against peptide 1 (SEQ ID NO. 2) to the assigned values of the same patient samples measured using the Roche Elecsys® assay.

FIG. 15 shows the same data as FIG. 14, here only including samples with a measured NT-proBNP concentration lower than 1000 ng/L.

The inventors have shown that it is feasible to measure NT-proBNP in a particle-enhanced turbidimetric immunoassay. In the Roche Elecsys® sandwich immunoassay, the immunoassay antibodies are however influenced by glycosylation moieties, as described in Rosjo et al. Full correlation between the assays of the present innovation and the Roche Elecsys® NT-proBNP immunoassay cannot be expected, and due to said interference, differences between the two assays must be expected.

The turbidimetric assay was also run on another instrument, the Architect c4000 clinical analyzer, with necessary adjustments of the wavelength, reading interval etc. Calibrator values were adjusted to align with the Roche method.

TABLE 7

PETIA parameters in Abbot Architect c4000

| Parameter | Setting |
| --- | --- |
| Sample volume [µL] | 5 |
| R1: Assay buffer volume [µL] | 150 |
| R2: Reagent volume [µL] | 25 |
| Wavelength [nm] | 548 |
| Reading time | cycle 18-18 (blank) 32-33 (reading) |

The results confirmed that the method is applicable to being run on different platforms. FIG. 16 shows that sample measurements recorded on the Mindray® and Architect instruments correlate very well.

Example 8. Mixture of Immunoparticles

An assay using a mixture of immunoparticles was also tested in the same set-up as disclosed in Example 7, with the difference that a mix of two different batches of immunoparticles was used to make the reagent buffer R2: 200 nm latex nanoparticles coated with antibodies against the peptide of SEQ ID NO. 2 (Lot 46), and 200 nm latex nanoparticles coated with antibodies against the peptide of SEQ ID NO. 3 (Lot 49) were mixed in the ratio 1:0.6.

The assay buffer R1 had the following composition: 12.5 mM MOPS, 210 mM NaCl, 0.4% PEG, 0.1% IgG, 0.1% ProClin™, pH 7.2. The assay was run on a Mindray® BS-400 instrument using exactly the same settings as shown in Table 6.

FIG. 17 shows that immunoparticles coated with antibodies raised against Peptide 1 (SEQ ID NO. 2) can be mixed with immunoparticles coated with antibodies raised against Peptide 2 (SEQ ID NO. 3) and produce a functioning assay. The response correlates linearly with increasing concentrations of NT-proBNP, a set of calibrators produced from native antigen by mixing patient samples as described in Example 6.

In FIG. 18, the results (ng/I) of 14 turbidimetric measurements of NT-proBNP are compared to the assigned values of the same patient samples measured using the Roche Elecsys® assay. The results show that immunoparticles coated with antibodies raised against different peptides can be successfully mixed, resulting in a functional assay. The results further indicate that the mixture of immunoparticles is binding to multiple non-glycosylated regions of the NT-proBNP molecules, thereby resulting in a stronger turbidimetric signal and the detection also of lower concentrations.

Without further elaboration, it is believed that a person skilled in the art can, using the present description, including the examples, utilize the present invention to its fullest extent. Also, although the invention has been described herein with regard to its preferred embodiments, which constitute the best mode which is set forth in the claims appended hereto.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Blirup-Jensen, S. et al., Protein Standardization IV: Value Transfer Procedure for the Assignmnt of Serum Protein Values from a Reference Preparation to a Target Material, Clin Chem Lab Med 2001; 39(11): 1110-1122)

Dolgin M, Association NYH, Fox AC, Gorlin R, Levin R I, New York Heart Association. Criteria Committee. Nomenclature and criteria for diagnosis of diseases of the heart and great vessels. 9th ed. Boston, Mass.: Lippincott Williams and Wilkins; Mar. 1, 1994.

Geysen, H. M et al., Use of peptide synthesis to probe viral antigens for epitopes to a resolution of a single amino acid, PNAS, Jul. 1, 1984 81 (13) 3998-4002

Halfinger, B. et al., Unravelling the Molecular Complexity of 0-Glycosylated Endogenous (N-Terminal) pro-B-Type Natriuretic Peptide Forms in Blood Plasma of Patients with Severe Heart Failure. Clinical Chemistry. 2017, Vol. 63, 1

Harlow et al. (Eds.), Antibodies: A Laboratory Manual; Cold Spring Harbor Laboratory; Cold Spring Harbor, N.Y. (1988), Chapter 6

Januzzi et al., NT-proBNP testing for diagnosis and short-term prognosis in acute destabilized heart failure: an international pooled analysis of 1256 patients. Eur Heart J 2006; 27: 330-37

Langedijk et al. (2011) Helical peptide arrays for lead identification and interaction site mapping, Analytical Biochemistry 417:149-155

Rosjo et al., Influence of glycosylation on diagnostic and prognostic accuracy of N-terminal pro-B-type natriuretic peptide in acute dyspnea: data from the Akershus Cardiac Examination 2 Study, Clin Chem, 2015 August; 61(8): 1087-97. doi: 10.1373/clinchem.2015.239673. Epub 2015 Jun. 8.

Saenger, A. K. et al., Specificity of B-Type Natriuretic Peptide Assays: Cross-Reactivity with Different BNP, NT-proBNP, and proBNP Peptides, Clinical Chemistry, 63:1 (2017) 351-358

Schellenberger, U. et al., The precursor to B-type natriuretic peptide is an 0-linked glycoprotein, Arch Biochem Biophys. 2006 Jul. 15; 451(2):160-6. Epub 2006 Apr. 19

Semenov et al., Processing of proBNP is suppressed by O-glycosylation on the region close to the cleavage site, Clin Chem, 2009, 55(3): 489-498

TechNotes|Human ProBNP, BNP and NT-proBNP, HyTest Ltd., January 2019, https://shop.hytest.fi/spree/products/2932/Human_proBNP_BNP_and NT-proBNP_TechNotes.pdf?1560757320, downloaded 07.08.2019

Timmerman et al., (2007) Functional reconstruction and synthetic mimicry of a conformational epitope using CLIPS™ technology, J. Mol. Recognit. 20:283-299

The invention claimed is:

1. A method for determining the concentration of N-terminal pro-brain natriuretic peptide (NT-proBNP) in a sample, said method comprising the following steps:
   (i) contacting the sample with at least one polyclonal antibody which specifically binds to NT-proBNP within the amino acid sequence of SEQ. ID. NO. 4, SEQ. ID. NO 5, SEQ. ID. NO. 6, SEQ. ID. NO. 7, SEQ. ID. NO. 8, SEQ. ID. NO. 9, or SEQ. ID. NO. 10, and conducting a step of calibration using a calibrator comprising a known concentration of a substance chosen from a peptide having the amino acid sequence of SEQ. ID. NO. 4, SEQ. ID. NO 5, SEQ. ID. NO. 6, SEQ. ID. NO. 7, SEQ. ID. NO. 8, SEQ. ID. NO. 9, or SEQ. ID. NO. 10;
wherein said at least one polyclonal antibody is immobilized to a particle, and wherein the calibrator is non-glycosylated; and
   (ii) detecting a change in reflectance, scattering or transmittance of the sample wherein said change is indicative of the concentration of NT-proBNP in the sample.

2. The method according to claim 1, wherein said at least one polyclonal antibody specifically binds to NT-proBNP within the amino acid sequence of SEQ. ID. NO 5, SEQ. ID. NO. 7, or SEQ. ID. NO. 8.

3. The method according to claim 2, wherein said at least one polyclonal antibody specifically binds to the amino acids of SEQ. ID. NO. 8.

4. The method according to claim 1, wherein said at least one polyclonal antibody is bound to a latex particle having an average size in the range of 150-300 nm.

5. The method of claim 1, further comprising, on the basis of said concentration of NT-proBNP in the sample, diagnosing, monitoring, or stratifying patients with heart failure or subjects at risk of developing heart failure.

6. The method according to claim 1, wherein said at least one polyclonal antibody binds specifically to NT-proBNP with a $K_D$ to NT-proBNP of less than 10.0E-09 M.

7. The method according to claim 6, wherein said at least one polyclonal antibody binds specifically to NT-proBNP with a $K_D$ to NT-proBNP of less than 5.0E-09 M.

8. The method according to claim 7, wherein said at least one polyclonal antibody binds specifically to NT-proBNP with a $K_D$ to NT-proBNP of less than 2.0E-09 M.

9. The method according to claim 1, wherein said at least one polyclonal antibody binds specifically to a peptide having the amino acid sequence of SEQ. ID. NO 5, SEQ. ID. NO. 7, or SEQ. ID. NO. 8 with a $K_D$ of less than 5.0E-09 M.

10. The method according to claim 9, wherein said at least one polyclonal antibody binds specifically to a peptide having the amino acid sequence of SEQ. ID. NO 5, SEQ. ID. NO. 7, or SEQ. ID. NO. 8 with a $K_D$ of less than 2.0E-09 M.

* * * * *

SEQUENCE LISTING

<160> NUMBER OF SEQ ID NOS: 10

<210> SEQ ID NO 1
<211> LENGTH: 76

<212> TYPE: PRT
<213> ORGANISM: Human

<400> SEQUENCE: 1

```
His Pro Leu Gly Ser Pro Gly Ser Ala Ser Asp Leu Glu Thr Ser Gly
1               5                   10                  15
Leu Gln Glu Gln Arg Asn His Leu Gln Gly Lys Leu Ser Glu Leu Gln
            20                  25                  30
Val Glu Gln Thr Ser Leu Glu Pro Leu Gln Glu Ser Pro Arg Pro Thr
        35                  40                  45
Gly Val Trp Lys Ser Arg Glu Val Ala Thr Glu Gly Ile Arg Gly His
    50                  55                  60
Arg Lys Met Val Leu Tyr Thr Leu Arg Ala Pro Arg
65                  70                  75
```

<210> SEQ ID NO 2
<211> LENGTH: 26
<212> TYPE: PRT
<213> ORGANISM: Recombinant

<400> SEQUENCE: 2

```
Ser Ala Ser Asp Leu Glu Thr Ser Gly Leu Gln Glu Gln Arg Asn His
1               5                   10                  15
Leu Gln Gly Lys Leu Ser Glu Leu Gln Val
            20                  25
```

<210> SEQ ID NO 3
<211> LENGTH: 14
<212> TYPE: PRT
<213> ORGANISM: Recombinant

<400> SEQUENCE: 3

```
Ile Arg Gly His Arg Lys Met Val Leu Tyr Thr Leu Arg Ala
1               5                   10
```

<210> SEQ ID NO 4
<211> LENGTH: 5
<212> TYPE: PRT
<213> ORGANISM: Human

<400> SEQUENCE: 4

```
Ser Ala Ser Asp Leu
1               5
```

<210> SEQ ID NO 5
<211> LENGTH: 14
<212> TYPE: PRT
<213> ORGANISM: Human

<400> SEQUENCE: 5

```
Asp Leu Glu Thr Ser Gly Leu Gln Glu Gln Arg Asn His Leu
1               5                   10
```

<210> SEQ ID NO 6
<211> LENGTH: 7
<212> TYPE: PRT
<213> ORGANISM: Human

<400> SEQUENCE: 6

```
Asn His Leu Gln Gly Lys Leu
1               5
```

```
<210> SEQ ID NO 7
<211> LENGTH: 8
<212> TYPE: PRT
<213> ORGANISM: Human

<400> SEQUENCE: 7

Ser Ala Ser Asp Leu Glu Thr Ser
1               5

<210> SEQ ID NO 8
<211> LENGTH: 6
<212> TYPE: PRT
<213> ORGANISM: Human

<400> SEQUENCE: 8

Glu Thr Ser Gly Leu Gln
1               5

<210> SEQ ID NO 9
<211> LENGTH: 7
<212> TYPE: PRT
<213> ORGANISM: Human

<400> SEQUENCE: 9

Gly Lys Leu Ser Glu Leu Gln
1               5

<210> SEQ ID NO 10
<211> LENGTH: 6
<212> TYPE: PRT
<213> ORGANISM: Human

<400> SEQUENCE: 10

Gly Leu Gln Glu Gln Arg
1               5
```